United States Patent [19]

Spivey et al.

[11] Patent Number: 5,528,043
[45] Date of Patent: Jun. 18, 1996

[54] X-RAY IMAGE SENSOR

[75] Inventors: Brett Spivey; Peter Martin, both of Encinitas; Lee Morsell, Del Mar; Eugene Atlas, Carlsbad, all of Calif.; Anthony Pellegrino, New Fairfield, Conn.

[73] Assignee: Thermotrex Corporation, San Diego, Calif.

[21] Appl. No.: 426,691

[22] Filed: Apr. 21, 1995

[51] Int. Cl.⁶ .............................. G01T 1/24; H01L 27/14
[52] U.S. Cl. .................. 250/370.09; 250/580; 250/208.1
[58] Field of Search ........................ 250/370.08, 370.09, 250/370.14, 580, 208.1; 378/98.8

[56] References Cited

U.S. PATENT DOCUMENTS

| | | | |
|---|---|---|---|
| 4,841,348 | 6/1989 | Shizukuishi et al. | 257/226 |
| 5,235,195 | 8/1993 | Tran et al. | |
| 5,319,206 | 6/1994 | Lee et al. | 250/370.09 |

*Primary Examiner*—Carolyn E. Fields
*Assistant Examiner*—Edward J. Glick
*Attorney, Agent, or Firm*—John R. Ross

[57] ABSTRACT

This invention provides an imaging system for producing images from electromagnetic radiation such as x-rays. The system includes a detector comprised of a radiation-absorbing layer sandwiched between an array of CMOS integrated circuits (which we call pixel circuits) and a surface electrode layer transparent to the radiation. Each of the pixel circuits in the array has a charge collecting electrode. An external voltage applied between the surface electrode layer and the charge collecting electrodes produces an electric field across the thickness of the absorbing layer. Radiation passing through the transparent surface electrode layer is absorbed in the absorbing layer creating electron/hole pairs in the absorbing layer. A portion of the liberated holes (or electrons) migrates under the influence of the electric field toward the charge collecting electrodes, which collect the holes and store them as charges on small capacitors located within each circuit. This process results in a discrete distribution of stored voltages across the array proportional to the distribution of radiation photons incident on the absorbing layer. Circuitry in each pixel provides for the voltage on each pixel capacitor to be recorded via readout circuitry and permits the resetting of the pixel capacitors. Preferred embodiments provide fine resolution with a large number of pixels with dimensions about the size of the thickness of human hair.

49 Claims, 17 Drawing Sheets

X-RAY IMAGE SENSOR

The present invention relates to imaging devices and specifically to devices forming images from radiation.

BACKGROUND OF THE INVENTION

Film-screen x-ray imaging devices employing photographic film are widely used for medical imaging. However, the film is often overexposed in some areas and underexposed in other areas due to the limited range of contrast of the film combined with the thickness and composition variations of the tissue across the image. Discrimination of contrast differences of soft tissue in the overexposed and underexposed areas of the film can be difficult. This problem is especially apparent in film-screen mammography.

Attempts have been made at replacing film with electronic image sensors. Potential advantages of electronic image sensors over film include more accurate measurement of x-ray intensity over greater ranges, ability to digitize the image data, ease of archiving and transmitting image data, and improved display capabilities.

However, widespread clinical deployment of digital x-ray radiology has been hampered by the lack of a relatively inexpensive, compact, digital x-ray image sensor of sufficient image size and resolution. Present digital x-ray imaging systems typically use a fluorescing plate that converts each x-ray photon into a large number of visible light photons to produce a visible light image. The visible light image is then imaged onto an optical image sensor such as a CCD. The imaging performance of these techniques is degraded by relatively low x-ray to visible light conversion efficiencies, low collection efficiencies of the light photons, additional quantum noise from the light photons, and loss of resolution due to light spreading in the x-ray to visible light converter.

It is known that selenium is a photoconductive substance, i.e. x-ray photons absorbed in a layer of selenium exposed to an electric field will create a number of electron/hole pairs permitting a current to flow through the otherwise insulating layer. Xerox Corporation developed an x-ray imaging device in which an x-ray induced charge distribution on a selenium-coated aluminum plate is recorded with a paper/toner process. Philips Corporation presently markets a chest x-ray imager in which an x-ray induced charge distribution on a selenium-coated aluminum plate is recorded with scanning electrometers.

Complimentary metal oxide semiconductor (CMOS) fabrication technology is a well established industry which involves fabricating integrated circuits on and in the upper surface of a wafer of crystalline silicon. CMOS technology utilizes the silicon of the substrate wafer as the semiconductor material for transistor fabrication. The high mobility of charge carries in single-crystal silicon results in fast, compact, low-noise circuitry. Wafers with dimensions as large as six inches are available for large area CMOS circuits.

Thin film transistor (TFT) technology is an emerging semiconductor fabrication technology in which transistors are fabricated using a thin film of semiconductor material such as amorphous silicon, polycrystalline silicon or amorphous cadmium selenide deposited on an insulating substrate. An advantage of TFT technology is the potential for large area circuits. However, the disordered molecular structure of these thin films leads to low charge mobility which limits performance. In comparison with CMOS circuits, TFT circuits are generally slow and noisy with large leakage currents.

Various approaches are presently being proposed and investigated for directly acquiring a digital x-ray image. For example, Zhao and Rowlands (Proc. SPIE 1993; 1896:114–120) have proposed a readout array fabricated using cadium selenide TFT technology with an amorphous selenium coating. Tran et. al. disclose, in U.S. Pat. No. 5,235,195, TFT array circuits coated first with a "planarization" layer which in turn is coated with an energy-sensitive layer.

SUMMARY OF THE INVENTION

This invention provides a digital imaging system for producing images from electromagnetic radiation such as x-rays. The system includes a detector comprised of a radiation absorbing layer sandwiched between an array of CMOS integrated circuits (which we call pixel circuits) and a surface electrode layer transparent to the radiation. Each of the pixel circuits in the array has a charge collecting electrode. An external voltage applied between the surface electrode layer and the charge collecting electrodes produces an electric field across the thickness of the absorbing layer. X-ray photons pass through the transparent surface electrode layer and are absorbed in the absorbing layer creating electron/hole pairs in the absorbing layer. A portion of the liberated electric charge migrates under the influence of the electric field toward the charge collecting electrodes which collect charge and store these charges in small capacitors located within each circuit. This process results in a discrete distribution of stored voltages across the array proportional to the distribution of x-ray photons incident on the absorbing layer. Circuitry in each pixel provides for the voltage on each pixel capacitor to be recorded via readout circuitry and permits the resetting of the pixel capacitors. Advantages of this invention over the prior art TFT technology results from our exploitation of the many benefits of CMOS technology. These benefits include much better circuit performance as well as design flexibility which enables us to fabricate a pixel array and readout circuitry together on a single wafer of silicon.

DETAILED DESCRIPTION OF PREFERRED EMBODIMENTS

Basic Concept

Figure 1:
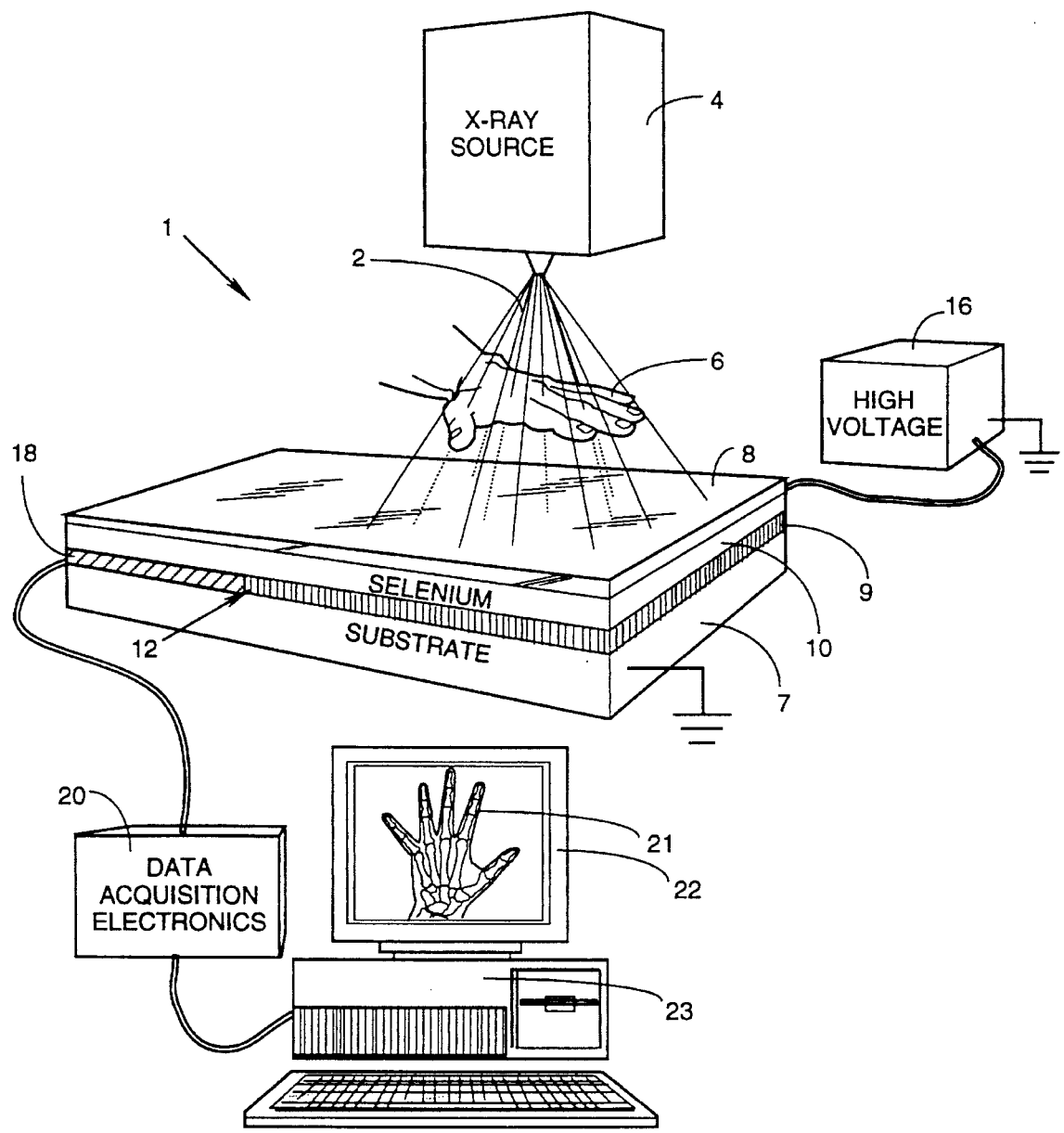
FIG. 1 shows the principal elements of a preferred embodiment of the present invention.

The basic concept on which this invention is based is depicted in FIG. 1 and FIGS. 2A through 2D. X-ray photons 2 produced by x-ray source 4 directed toward target 6 are either absorbed in or pass through target 6. Most of the x-ray photons which pass through target 6 also pass through transparent conductive layer 8 and are absorbed in absorbing layer 10 of x-ray sensor 1. Each absorbed x-ray photon in the process of being absorbed creates a large number of electron/hole pairs in absorbing layer 10 in the immediate vicinity of the absorption. An electric potential applied between the transparent conductive layer 8 and individual electrodes 14 in pixel array 9 by high voltage supply 16 forces holes from these electron/hole pairs to migrate to individual electrodes 14 located in pixel array 9. Pixel array 9 and readout circuit 18 together form electronic readout array 12 and are fabricated on and in the upper surface of a single substrate 7 of crystalline silicon. Electronic signals from the electronic readout array 12 representative of the x-ray photons absorbed in the absorbing layer 10 are directed from pixel array 9 through readout circuit 18 to data acquisition electronics 20. An image is computed from the data utilizing software in computer 23, and the x-ray image 21 of target 6 is displayed on monitor 22.

Figure 2A:
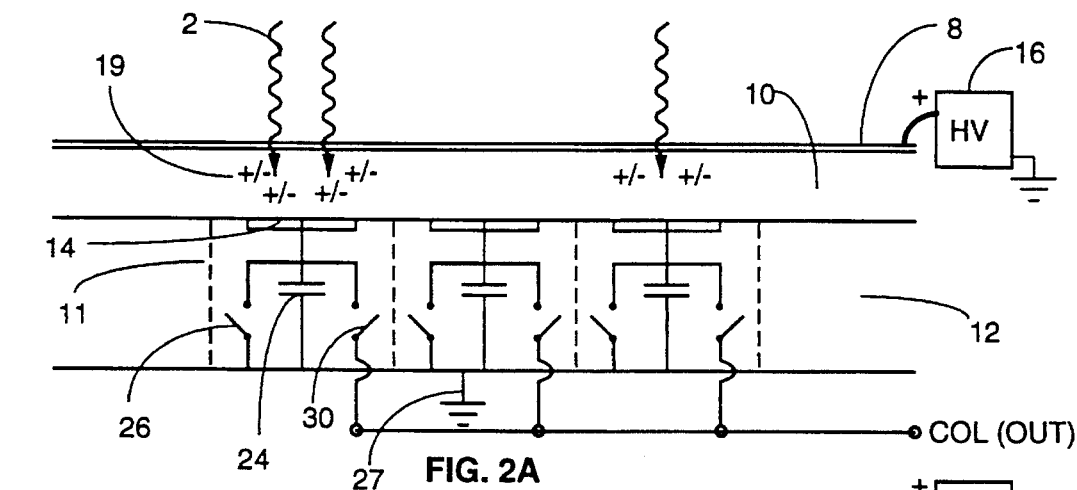
FIGS. 2A through 2D show the basic operating conditions of the invention.
Figure 2B:
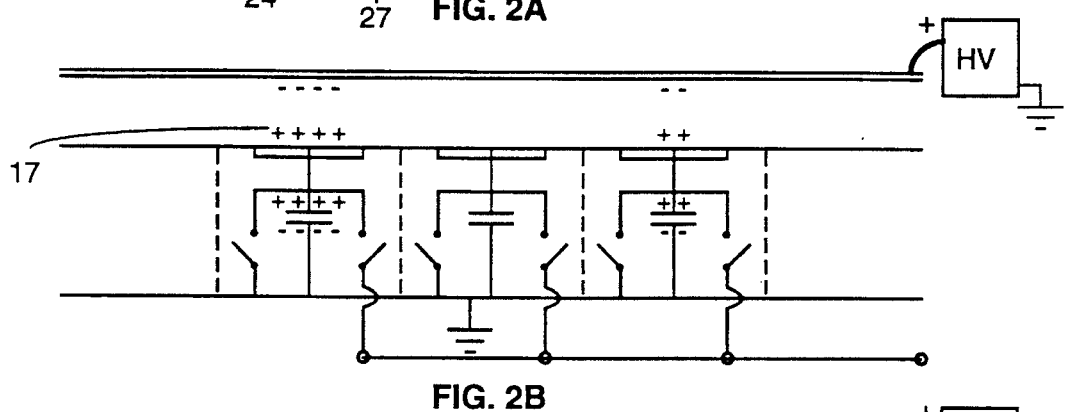
Figure 2C:
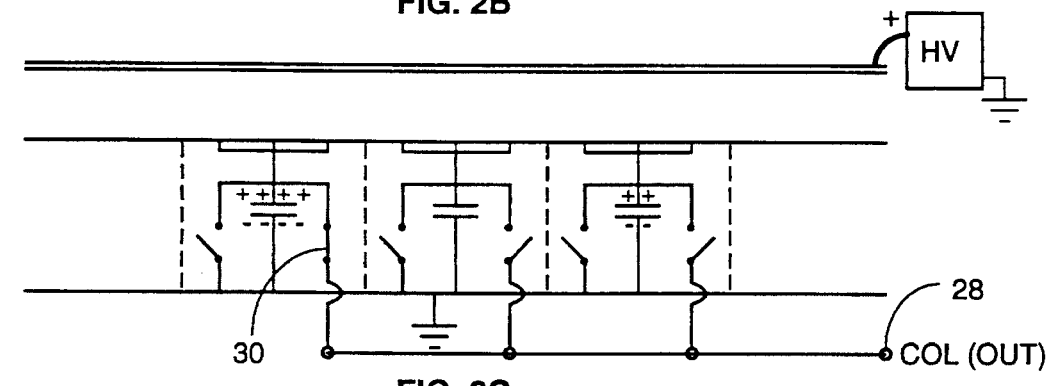
Figure 2D:
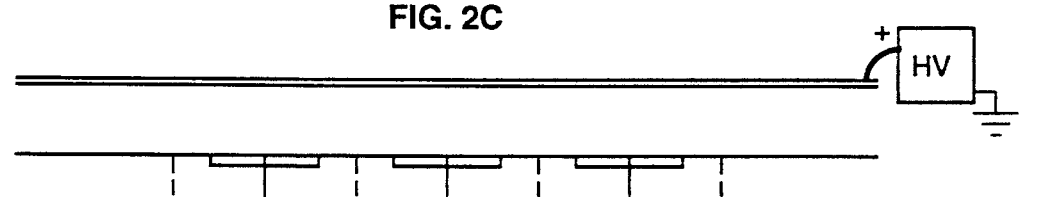

Each pixel in pixel array 9 is comprised of an individual electronic pixel circuit 11. Three of these pixel circuits 11 (segregated by dashed lines) are depicted in FIGS. 2A through 2D. FIG. 2A shows three x-ray photons 2 passing through transparent conductive layer 8 and being absorbed in the absorbing layer 10, each x-ray photon liberating electron/hole pairs in the immediate vicinity of the absorbed x-ray photon. A typical x-ray photon of intermediate x-ray energy will liberate several hundred electron/hole pairs. In FIGS. 2A–D we represent these several hundred hole pairs with two + and two − signs. As shown in FIG. 2B a positive electric potential applied to layer 8 forces the positive charges (holes) 17 to migrate downward to electrode 14 in pixel circuit 11. The voltage applied by source 16 is large enough so that there is very little lateral spreading of holes 17. Electrodes 14 collect the positive charges 17 and store the charges on capacitors 24, thus creating voltages across capacitors 24 which are proportional to the collected charges 17. As suggested by FIG. 2C, the collected positive charge 17 (and therefore the voltage across the capacitor 24) remains substantially constant after the x-ray source 4 is turned off. The voltage across each pixel capacitor 24 is non-destructively recorded by sequentially closing select switch 30 at each pixel circuit 11 in order to place the voltage on capacitor 24 onto output line 28 as Col (out). FIG. 2D shows that the collected charge 17 at all pixel circuits 11 can then be simultaneously drained to ground 27 by closing all of the reset switches 26 and shorting all of the capacitors 24 to ground 27.

The reader should note that in the above description conductive layer 8 is charged positive by high voltage supply 16. We could reverse the polarity of the sensor by charging conductive layer 8 negative. In this case electrons would be collected on electrodes 14 and the resulting negative charges could be utilized by similar electronic circuitry to produce images.

PROTOTYPE 8×16 PIXEL SENSOR

Figure 4:
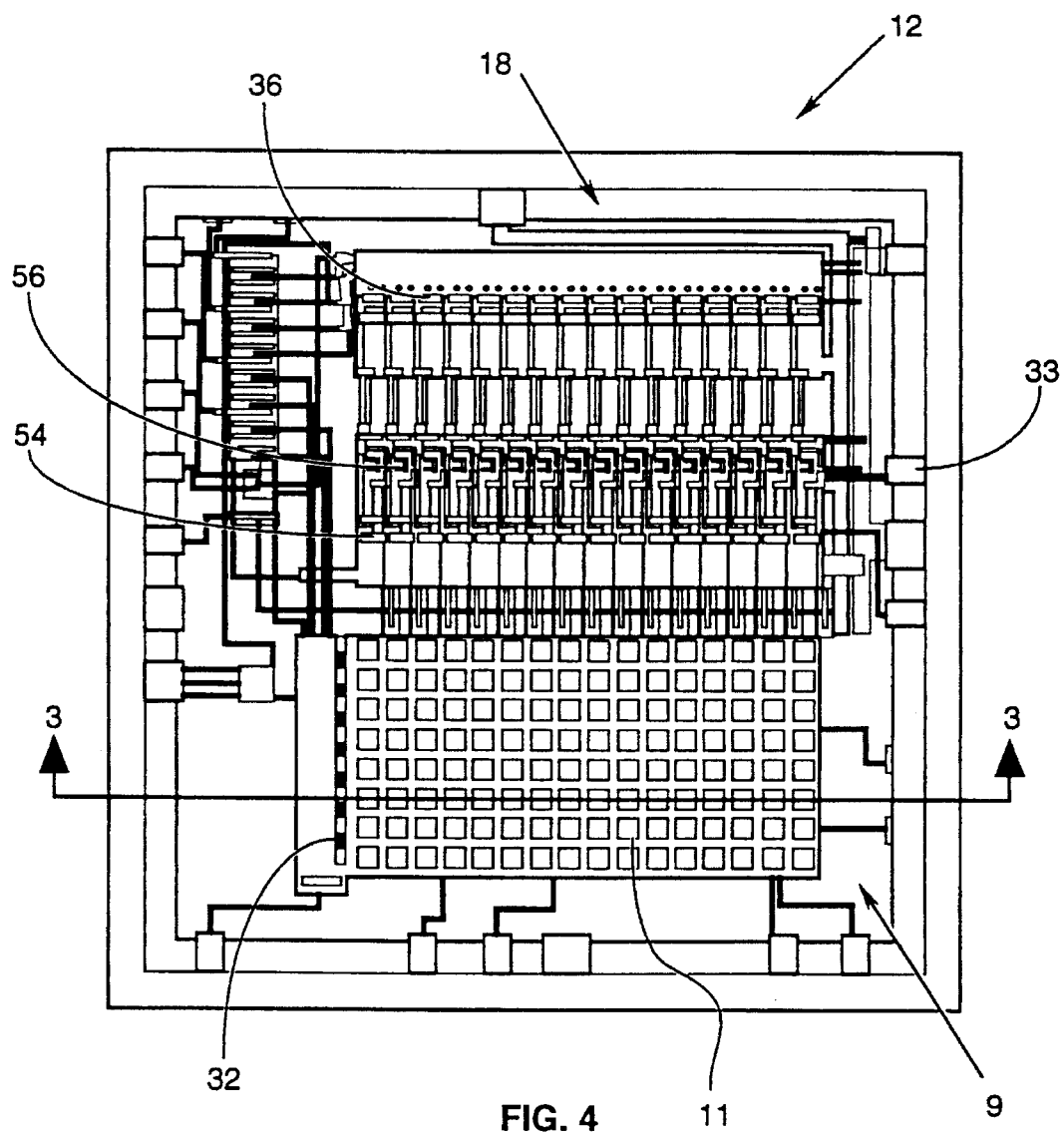
FIG. 4 shows a top view of the prototype electronic readout array.
Figure 3:
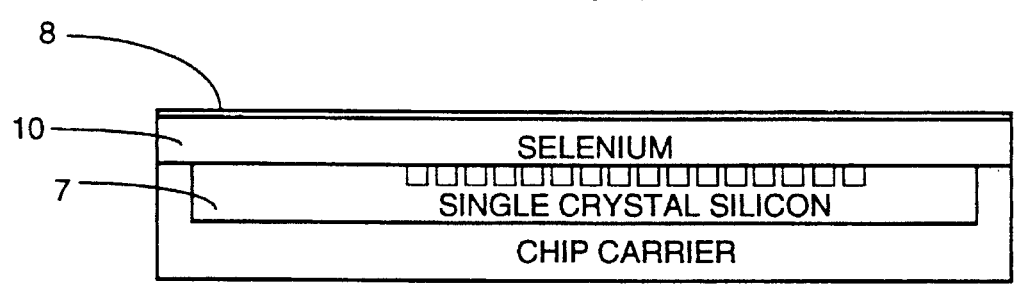
FIG. 3 is a cross sectional drawing of a prototype sensor fabricated and tested by the inventors.

FIGS. 3 and 4 are drawings of a first preferred embodiment of the present invention. This embodiment is a small 8×16 pixel prototype digital x-ray image sensor which has been fabricated and tested by the inventors and their fellow workers. The key elements include pixel array 9 with 128 pixel circuits 11 arranged in an 8×16 array. The size of each pixel circuit 11 is 66 microns ×66 microns (roughly the size of a human hair) resulting in a total imaging area of 0.5 mm×1 mm. Readout circuit 18 includes shift register 32 to select a row of pixel circuits 11 of the pixel array 9 for readout purposes. The readout circuit 18 also includes a shift register 36 for column selection, sample-and-hold circuits 54, bilateral switches 56, and pixel reset circuitry. Pixel array 9 and readout circuit 18, which together constitute electronic readout array 12, are fabricated in and on a substrate 7 of single crystal silicon. Wire bond pads 33 at the periphery of the electronic readout array 12 connect the readout circuit 18 to data acquisition electronics 20 as shown in FIG. 1. Pixel array 9 and readout circuit 18 are coated with a uniform layer of selenium 10 which is in turn coated with a conductive electrode layer 8. Electrode layer 8 is a very thin layer of silver which is substantially transparent to x-rays.

Sensor Circuitry

Figure 5:
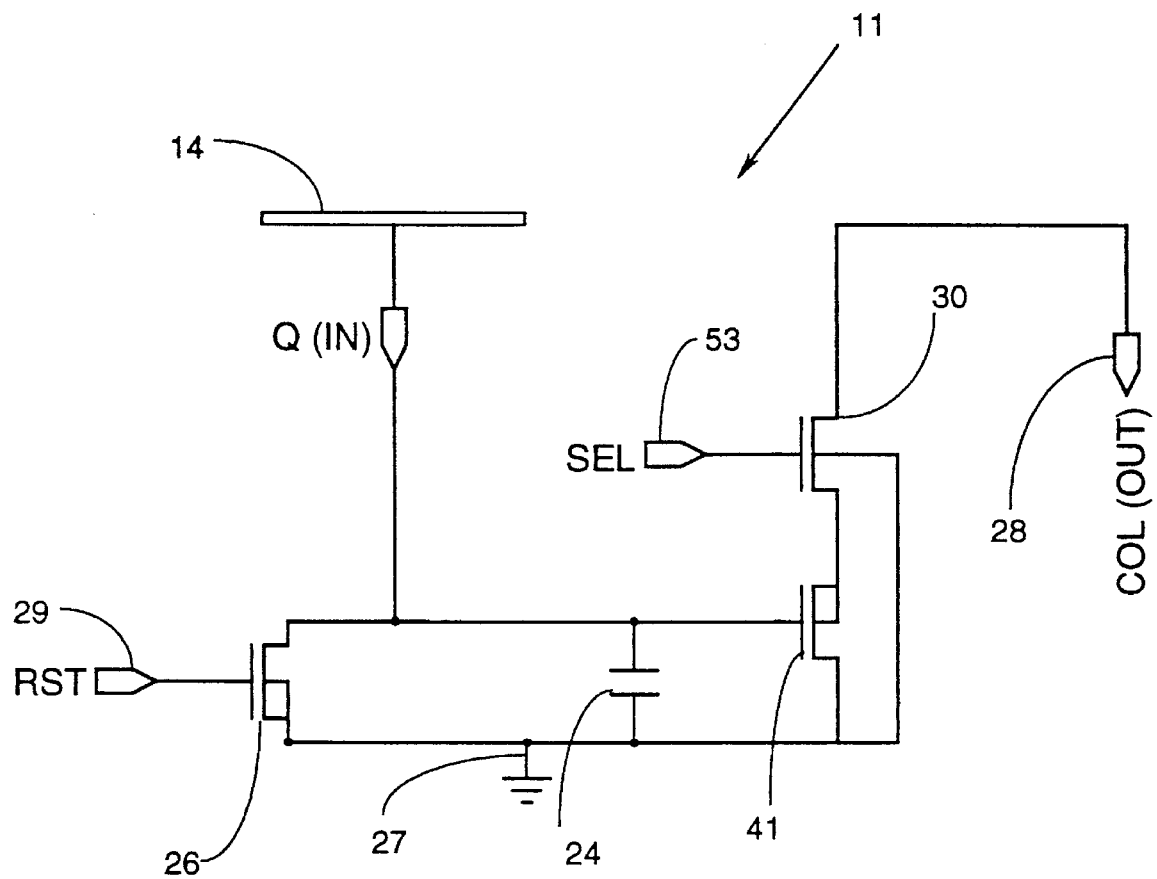
FIG. 5 is a circuit diagram of the elements in an individual pixel of the pixel array of the prototype readout array.

The circuit diagram of an individual pixel circuit 11 is displayed in FIG. 5. The charge Q (in) collected via electrode 14 charges 345 femptofarad capacitor 24 resulting in a voltage proportional to the collected charge Q (in). Source-follower transistor 41 acts a buffer for this voltage and allows for a non-destructive readout. A digital selection signal SEL applied at line 53 causes selection transistor 30 to turn on and connect the source of source-follower transistor 41 with column readout line 28. Then, source-follower transistor 41 acts together with current source transistor 110 at the edge of the array (see FIG. 8) to establish a voltage COL (out) on the column readout line 28 which follows the voltage on capacitor 24 with a small (approximately 0.5 Volt) positive voltage offset. After the charge on capacitor 24 has been read out, reset signal RST applied at line 29 enables reset transistor 26 to drain the charge from capacitor 24 to ground 27.

Figure 6:
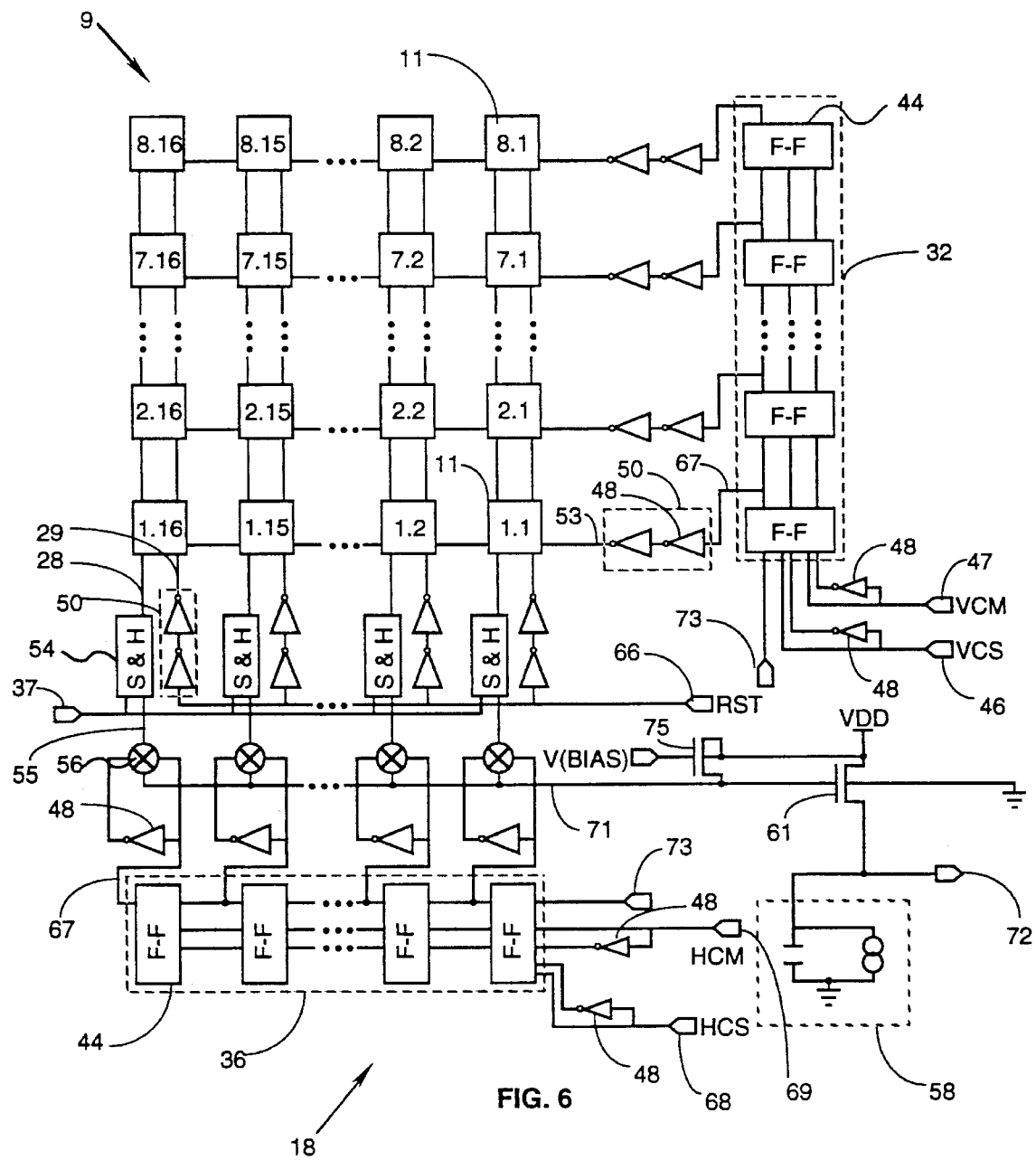
FIG. 6 is a schematic diagram of the electronic readout array utilized in the prototype embodiment.

The circuit diagram for the entire electronic readout array 12 can be described by reference to FIGS. 5 through 8. A schematic diagram for the electronic readout array 12, including the pixel array 9 and the readout circuit 18, is shown in FIG. 6. The primary circuit components include 128 identical pixel circuits 11 forming pixel array 9, row-select shift register 32, column-select shift register 36, sixteen sample-and-hold circuits 54, and sixteen bilateral switches 56.

The voltage on capacitor 24 of each pixel circuit 11 is sequentially recorded by the readout circuit 18 in the following manner. The entire first row (1.1, 1.2, . . . , 1.16) of pixel circuits 11 is selected when row-select shift register 32 activates row-select line 53 through buffer 50 which closes selection transistor 30 of each pixel 11 in the first row. Buffer 50 is comprised of two conventional inverter circuits 48. Each pixel circuit 11 in the first row is then sequentially and non-destructively read out in two steps. First, the voltages on column readout line 28 of the sixteen pixel circuits 11 (1.1, 1.2, . . . , 1.16) are simultaneously sampled each by a separate sample-and-hold circuit 54, when a digital signal is simultaneously applied to sample-and-hold circuits 54 at line 37. This sampling process produces a voltage at the output line 55 of each sample and hold circuit 54 (described below) which is identical to the voltage at each column readout line 28 except for a small (approximately 1 Volt) positive voltage offset. Second, the voltages at output lines 55 sampled by the sixteen sample-and-hold circuits 54 are sequentially connected to the output line 71 by bilateral switches 56, controlled by column-select shift register 36 (described below). The voltages present at output line 71, for which transistor 75 acts as a pull-up resistor, are buffered with source-follower transistor 61, which is supplied with drain current source 58. The resulting analog voltage signals at output line 72 are sent to data acquisition electronics 20. The readout process continues by sequential selection of the remaining 7 rows of pixel circuits 11, and voltage data from these rows is collected in a similar manner. There is no shifting of charge from the pixel circuits 11 to the readout circuit 18, as in the case of a CCD array. This feature of our CMOS array allows for a nondestructive readout and very low consumption of power.

The 8-cell row-select shift register 32 and 16-cell column-select shift register 36 have identical design features. The basic design, commonly used in CMOS logic circuits, comprises a string of master-slave flip-flop circuits 44, the output of one flip-flop 44 connected to input of the next flip-flop 44. The shift registers 32 and 36 sequentially shift a digital data signal (either high or low) from one flip-flop 44 to the next flip-flop 44 during each full cycle of a clock signals. Four synchronous, single-frequency clock lines connect in parallel to each flip-flop 44, one line each for the master clock CM, an inverted master clock CMB, a slave clock CS which is delayed one-half cycle from the master clock CM, and an inverted slave clock CSB. The input data line 73 is raised high during just one cycle of the clocks and then held low during subsequent clock pulses, and a single high signal moves along the shift register outputs 67 from one end of the shift register to the other. The row select shift register 32 is controlled by master clock VCM 47 and slave clock VCS 46 to sequentially select each row of the pixel array 9. The column-select shift register 36 is controlled by master clock HCM 69 and slave clock HCS 68 to sequentially select each bilateral switch 56.

Figure 7:
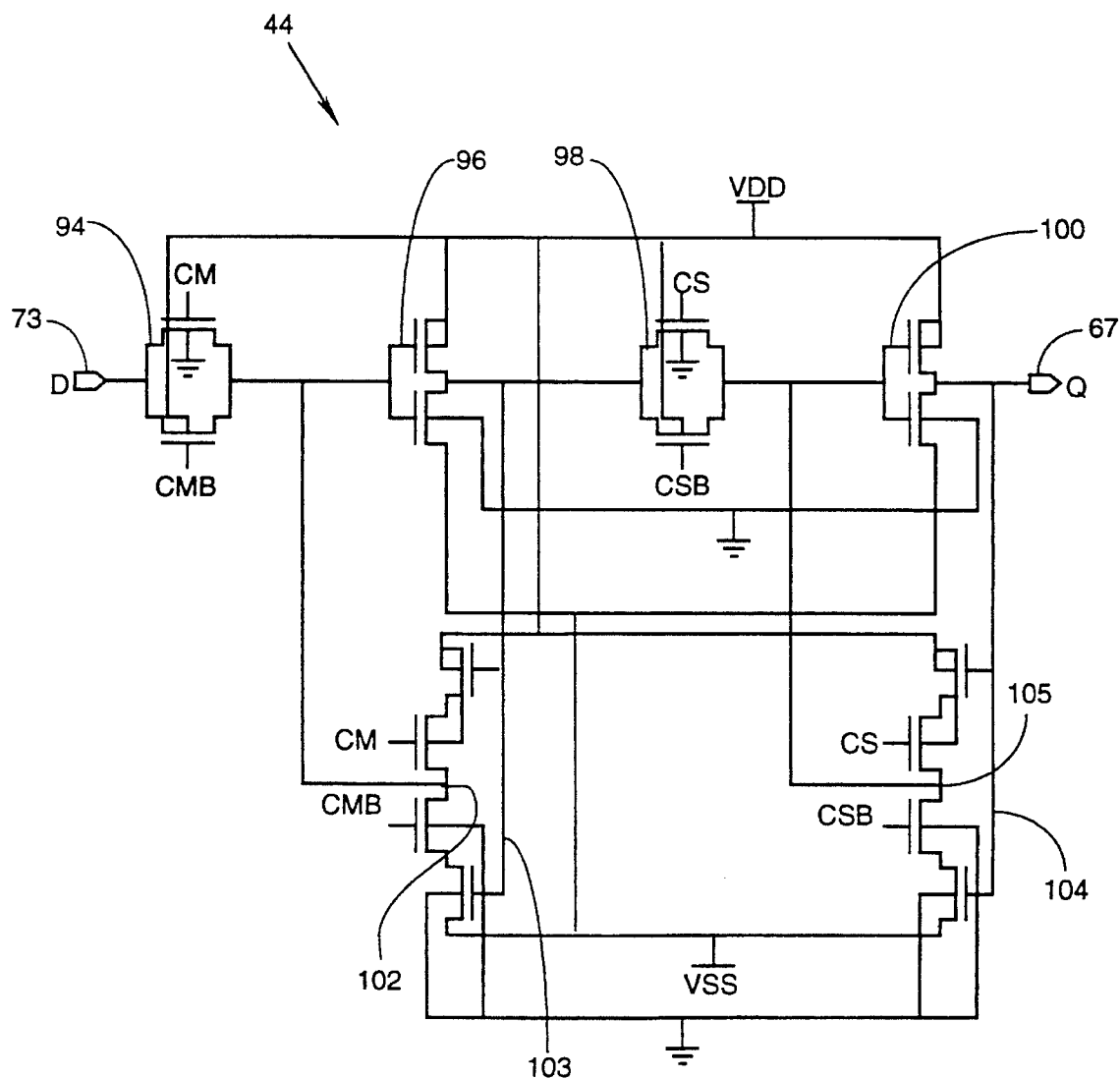
FIG. 7 is a circuit diagram of one cell of the shift register used in the readout circuitry.

FIG. 7 shows a circuit diagram of an individual master-slave flip-flop 44. The design, which is commonly used in CMOS logic circuitry, includes two identical flip-flop circuits in series, one flip-flop controlled by the master clock CM and CMB and the next flip-flop controlled by the slave clock CS and CSB. The master flip-flop consists of bilateral switch 94, controlled by master clock CM and CMB, connected in series with inverter 96. Tri-state inverter 102 provides feedback to allow bistable operation of the master flip-flop. The slave flip-flop consists of bilateral switch 98, controlled by slave clock CS and CSB, connected in series with inverter 100. Tri-state inverter 104 provides feedback to allow bistable operation of the slave flip-flop. A logic signal (high or low) at the D input 73 of bilateral switch 94 is sent to the input of bilateral switch 98 by a single transition of master clock CM. A single transition of slave clock CS, which is slightly delayed with respect to the master clock, then sends the logic signal at the input to bilateral switch 98 to the output Q 67.

Figure 8A:
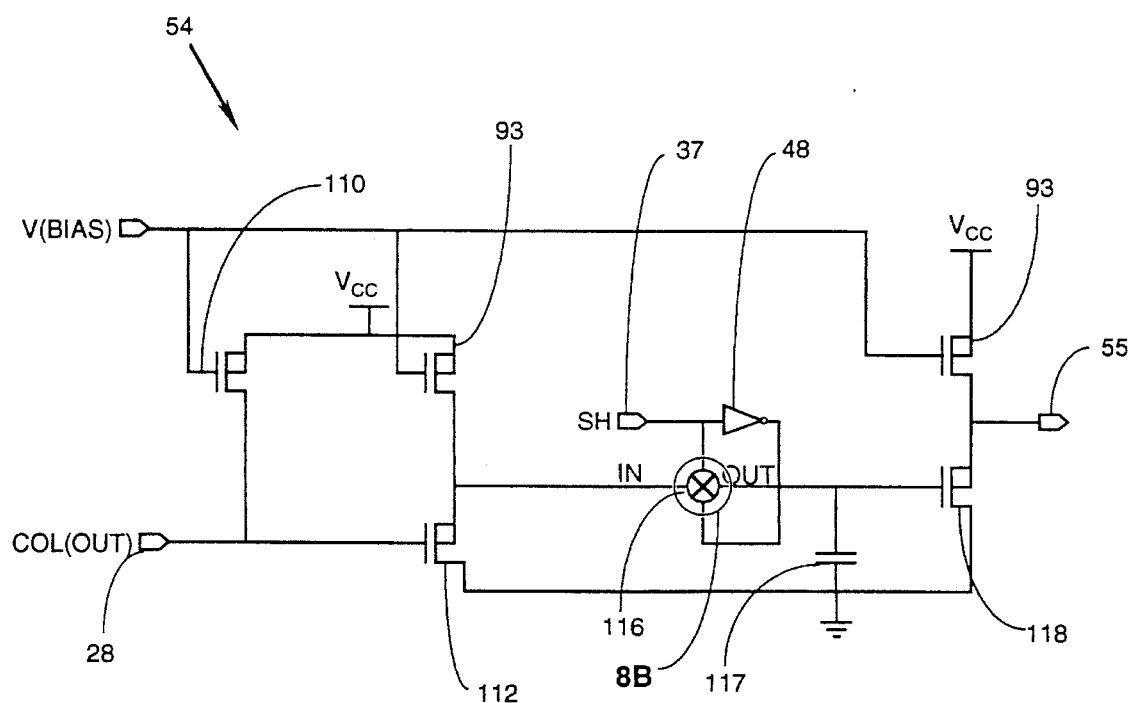
FIGS. 8A and 8B are circuit diagrams describing the sample-and-hold circuit used in the readout circuitry.
Figure 8B:
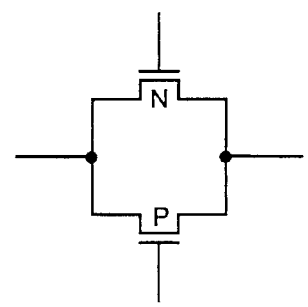

FIG. 8 is a schematic diagram of one of the sixteen sample-and-hold circuits 54 shown in FIG. 6. The basic design is commonly used in CMOS analog circuits. When a row of pixel circuits 11 is selected by shift register 32, selection transistors 30 in all the pixels in the row are turned on to connect the input 28 of each sample-and-hold circuit 54 with the source of source-follower transistor 41 on each pixel. Transistor 110, biased by external bias voltage V(bias), acts as a pull-up resistor for source-follower transistor 41 in pixel circuit 11 (see FIG. 5). Another source-follower transistor 112 in sample-and-hold circuit 54 buffers the voltage on input 28 and presents this voltage to the input of a bilateral analog switch 116. This switch 116, which allows current to flow in either direction when turned on by digital control signal SH 37, places the buffered voltage onto the 7.5 pF capacitor 117. Source-follower transistor 118 conveys the voltage on capacitor 117 to output line 55. Source-follower transistors 112 and 118 each have transistors 93, biased by external bias voltage V (bias), to act as pull-up resistors.

Sensor Fabrication

Electronic readout array 12 of the prototype sensor was fabricated using complimentary metal oxide semiconductor (CMOS) fabrication technology. CMOS fabrication technology is a well known integrated circuit fabrication technology and is described in many text books. A good description is also provided to in U.S. Pat. No. 3,356,858; by F. M. Wanlass (Issued Dec. 5, 1967). For our prototype device, the CMOS fabrication process begins with a wafer comprised of a single crystal of silicon, approximately 500 microns thick, which is doped with an electron-acceptor impurity, such as boron, in order to produce a p-type substrate 7. Field effect transistors (FET's) are produced on and in the upper one micron layer of the p-type silicon substrate 7. These transistors provide the basic circuit elements of the electronic readout array 12, shown in FIGS. 5 through 8, including digital and analog switches, current source transistors, and source-follower transistors. Passive electrical circuit components such as capacitors, resistors, transistor gates, and electrically conductive lines to connect the circuit components, are fabricated by adding alternate patterned layers of electrical insulators and conductors.

A typical CMOS process begin with the addition of patterned layers of electron-acceptor or electron-donor impurities, in substrate 7 to produce patterns of p-type or n-type regions, respectively. A p-type region has a surplus of mobile holes and an n-type region has a surplus of mobile electrons in the silicon crystal. Then, different patterned layers of insulating oxide, conductive polysilicon, and conductive metal are sequentially placed on substrate 7. The fabrication of each of these patterned layers requires many steps, including the coating the substrate with the specific layer, coating the layer with a light-sensitive organic film called photoresist, projecting a mask pattern onto the photoresist to sensitize it, selectively dissolving the photoresist to have a pattern matching the projected pattern, etching the layer below the photoresist in the open regions of the photoresist pattern, and finally, removing the remaining photoresist. The patterned n-type and p-type regions are produced by ion implantation through a patterned oxide layer.

Figure 9:
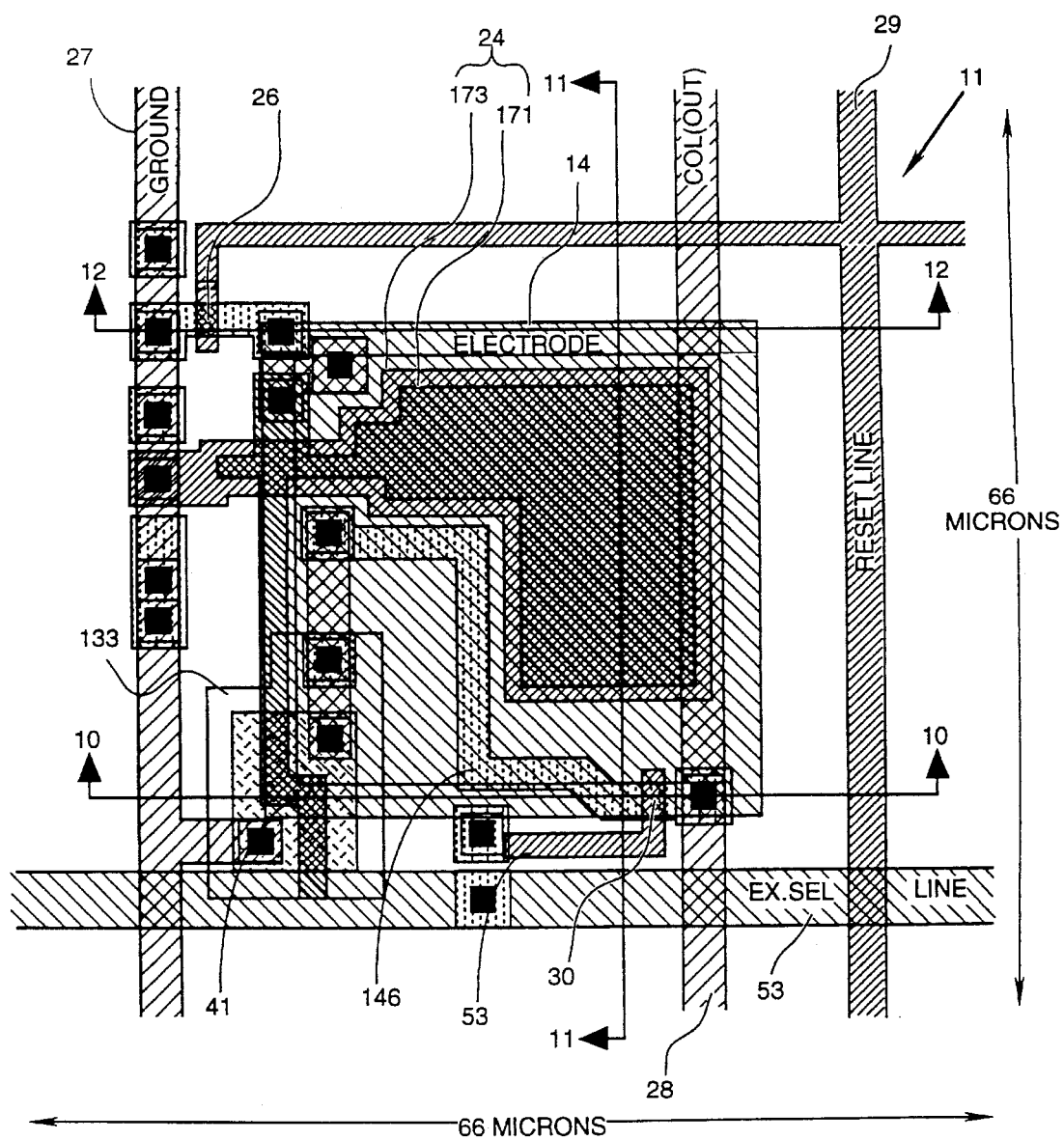
FIG. 9 shows a top view of the actual layout of the elements in an individual pixel of the pixel array.
Figure 10:
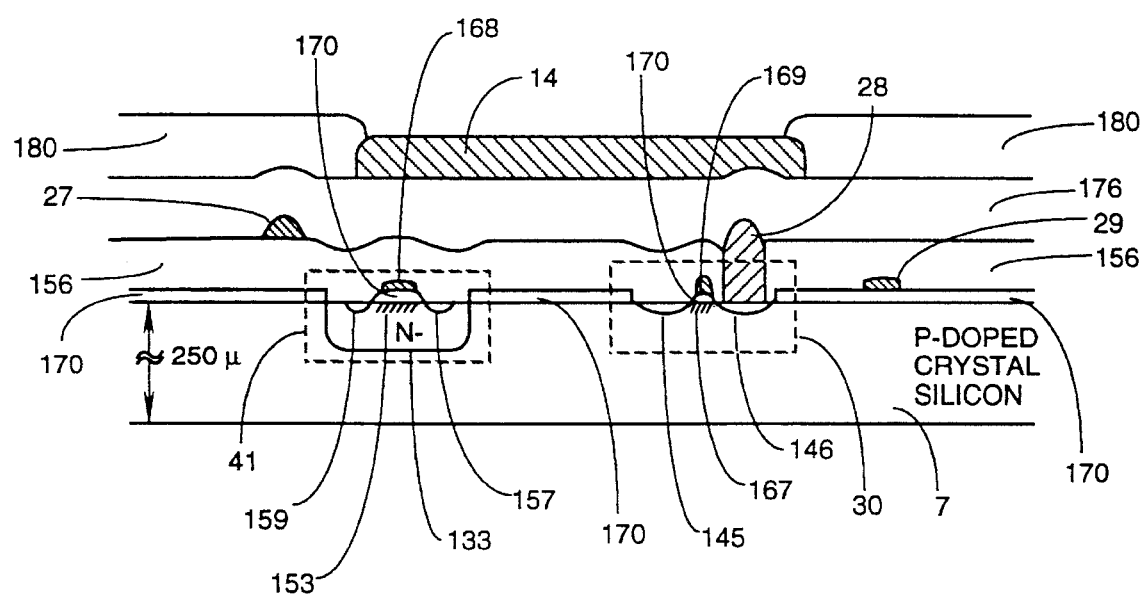
FIGS. 10–12 show three cross sections of the actual layout in an individual pixel of the pixel array.
Figure 11:
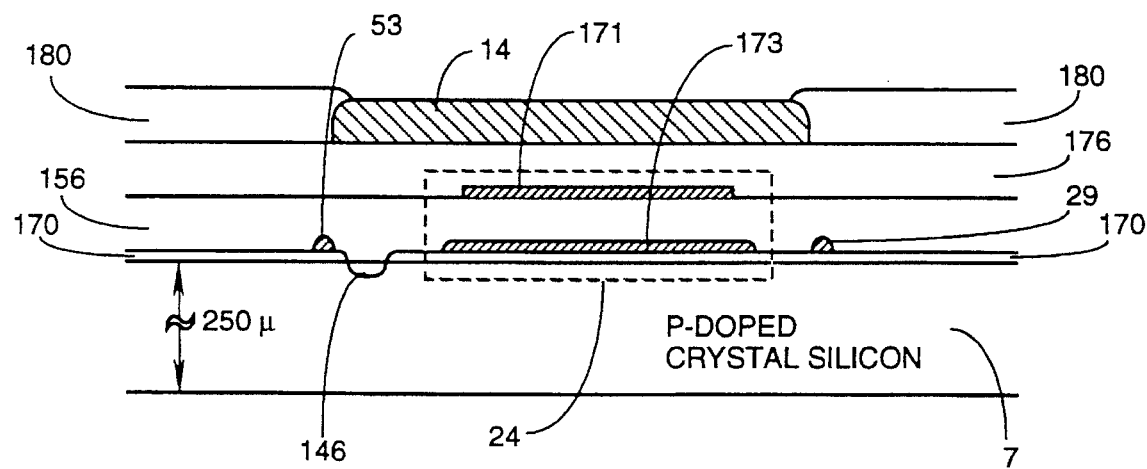
Figure 12:
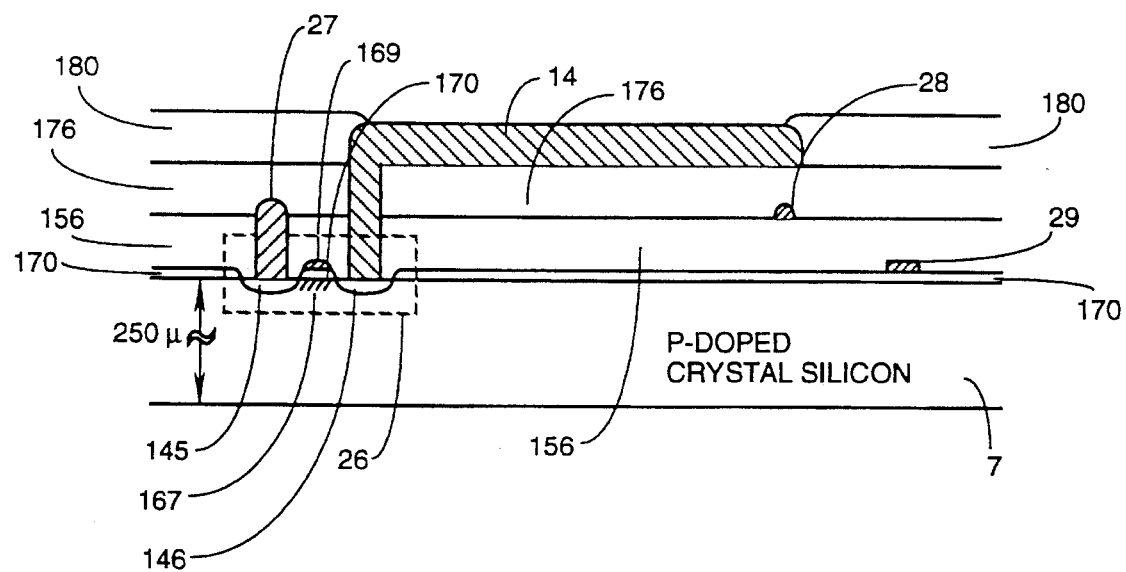

A top view of the layout of the electronic readout array 12 is shown in FIG. 4. This figure shows the layout of the 128 pixel circuits 11 of the pixel array 9, and the readout circuitry 18 including the row-select shift register 32, column-select shift register 36, sample-and-hold circuits 54, analog switches 56, and wire bond pads 33. The layout of the circuitry associated with an individual pixel 11 is shown in FIGS. 9 through 12. FIG. 9 is a top view of pixel circuit 11 showing the circuit elements in each layer superimposed on each other. FIGS. 10 through 12 show three different cross-sectional slices of the layout. Together, these figures show the locations of the electrode 14, capacitor 24, source-follower transistor 41, external selection line 53, selection transistor 30, column readout line 28, reset line 29, reset transistor 26, and ground line 27.

Selection transistor 30 and reset transistor 26 are n-channel transistors and are fabricated using an ion implantation process to add an electron-donor impurity, such as phosphorus, to specific regions 146 and 145 in the p-type substrate 7, as shown in FIG. 10, in order to form n-type source 146 and n-type drain 145 on both sides of p-type region 167 in substrate 7. N-type source 146 and drain 145 each form n-p diodes with p-type substrate 7. These diodes are intentionally reverse-biased with respect to substrate 7 or have no voltage across them, thus preventing current from flowing between source 146 and drain 145. Transistor gate 169, fabricated from an electrically conductive layer of polysilicon, is separated from p-type region 167 by insulating oxide layer 170. A positive voltage between gate 169 and substrate 7 causes an electric field in region 167 which repels p-type carriers (holes) and attracts n-type carriers (electrons) into region 167. This charge redistribution converts region 167 from p-type to n-type, presents a continuous path of conducting n-type material between source 146 and drain 145, and allows selection transistor 30 to conduct electricity. When voltage between gate 169 and substrate 7 is zero or negative, these transistor do not conduct.

Source 146 and drain 145 regions of each transistor are connected to other circuit components by either conductive layers of polysilicon or conductive metal layers of aluminum. FIG. 12 shows source 146 and drain 145 of reset transistor 26 connected to electrode 14 (which is connected to capacitor 24 by a line not shown) and ground line 27, respectively. A positive voltage on gate 169 of reset transistor 26 allows capacitor 24 to be drained to ground 27. FIG. 10 shows source 146 of selection transistor 30 connected to Col(out) line 28. Drain 145 of selection transistor 30 is connected to source 153 of source-follower transistor 41 through an electrical path not shown in FIG. 12. A positive voltage on gate 169 of selection transistor 30 allows Col(out) line 28 to be electrically connected to source 153 of source-follower transistor 41. Drain 155 of transistor 41 is connected to ground line 27.

FIG. 10 shows that source-follower transistor 41, a p-channel transistor, requires a substrate of n-type silicon which is provided by n-well 133. N-well 133 is an island of n-type material created in p-type silicon substrate 7 by an ion implantation process. N-well island 133 forms an n-p diode with substrate 7 and is kept at a positive voltage with respect to substrate 7 to electrically isolate n-well 133 from substrate 7. Source 157 and drain 159 of transistor 41 are formed in n-well 133 by ion implantation of an electron-acceptor impurity, such as boron, to convert source 157 and drain 159 into p-type silicon. Transistor gate 168, fabricated from an electrically conductive layer of polysilicon, is separated from n-type region 133 by insulating oxide layer 170. A negative voltage on gate 168 causes an electric field in region 153 which repels n-type carriers (electrons) and attracts p-type carriers (holes) into region 153. This charge redistribution converts region 153 from n-type to p-type, presenting a continuous path of conducting p-type material between source 157 and drain 153, and allows transistor 41 to conduct electricity. Source 157 of transistor 41 is supplied a constant current from transistor 11 0, located in sample-and-hold circuit 54, when selection transistor 30 is turned on. The magnitude of the voltage at gate 168 (which represents the charge collected by electrode 14 and stored on capacitor 24) of source-follower transistor 41 controls the conductivity of transistor 41; hence the source of transistor 41 follows the voltage on capacitor 24 except for an offset voltage of approximately 0.5 Volts.

The passive electrical circuit components are produced by adding alternate patterned layers of electrical insulators and conductors. Electrical insulating layer 156 is provided by boron-phosphorus-silicon glass. The insulating layers 176 and 180 are provided by silicon dioxide ($SiO_2$). Doped polysilicon provides the electrically conducting parallel plates 171 and 173 of capacitor 24, as well as reset line 29. Aluminum-copper metal provides the electrically conducting column readout line 28, external selection line 53, ground line 27, and electrode 14.

The readout circuitry 18 is fabricated in a similar manner as the pixel circuit 11. N-channel and p-channel transistors are fabricated in the silicon substrate 7. Passive components are added in layers over the transistors.

Our prototype electronic readout arrays 12 were fabricated at ORBIT Semiconductor, Sunnyvale, Calif. This small scale design was fabricated on the same wafer with a number of other company's circuit designs, which resulted in an inexpensive fabrication run. We received thirty identical die, each die containing one electronic readout array 12 (see FIG. 4). The arrays were bonded to a conventional 28-pin chip carrier and wire bond pads 33 on each array were connected to the pins of the chip carrier by a conventional wire bonding technique. The wire bond pads 33 and wires were selectively coated with epoxy to protect them, leaving the pixel array 9 and readout circuitry 18 uncovered.

The prototype arrays were coated with amorphous selenium using a vapor deposition process. Selenium was deposited in various thicknesses up to 300 microns over the entire electronic readout array 12, including the pixel array 9 and the readout circuit 18. A 300 micron thickness provides good results for absorption of x-rays in the spectrum utilized in mammography applications from 17 keV to 28 keV. A 300 micron thick layer of selenium absorbs substantially all of the incident x-rays and protects the electronic readout array 12 from x-ray induced damage. However, the selenium layer 10 is thin enough so that the voltage from source 16 required for a given electric field does not become unreasonably high. The breakdown field strength for selenium is approximately 20 V/micron. A safe field strength is 5 V/micron, equivalent to 1500 volts across a 300 micron thick layer 10 of selenium.

The prototype sensors were then coated with a conductive electrode 8 of silver using a vapor deposition process. The silver thickness of 250 angstroms allows transmission of over 99.9 % of the incident x-ray photons in the range of 17 keV to 28 keV, and yet is thick enough to provide adequate electrical conductivity across its surface. The conductive electrode for each of the coated arrays was electrically connected to the chip carrier.

The prototype sensors were electrically connected to data acquisition electronics 20, which includes a circuit board to route power and clock lines to the sensor and to route output line 72 through an amplifier to a 12-bit analog-to-digital converter. A timing board generates the clocks required for the shift registers 32 and 36. The digital data from the analog-to-digital converter was sent to a 486 computer 23 which displays images 21 on monitor 22.

Figure 13A:
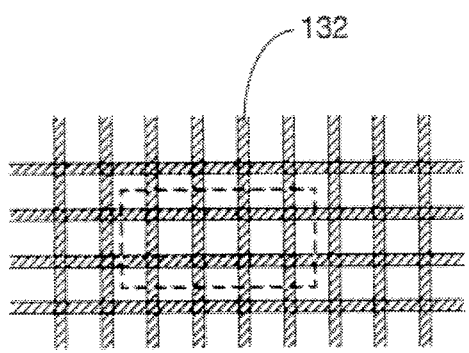
FIG. 13A and 13B are drawings of a wire screen and an x-ray image of the wire screen acquired with the first preferred embodiment.
Figure 13B:
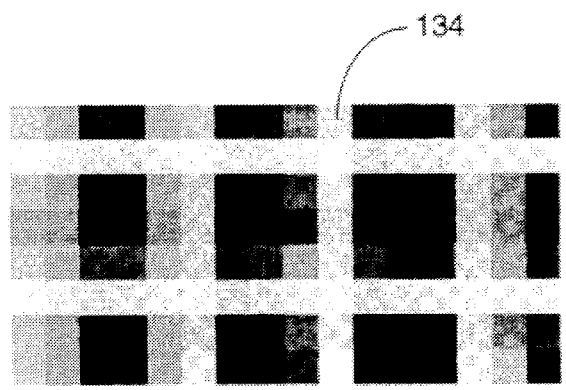
Figure 14A:
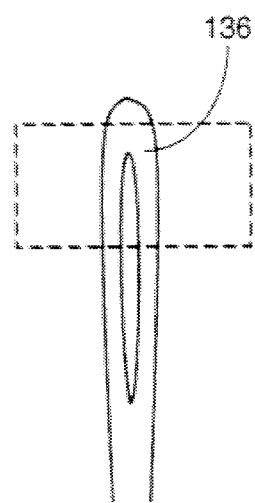
FIGS. 14A and 14B are drawings of a portion of sewing needle and an x-ray image of a portion of the needle acquired with the first preferred embodiment.
Figure 14B:
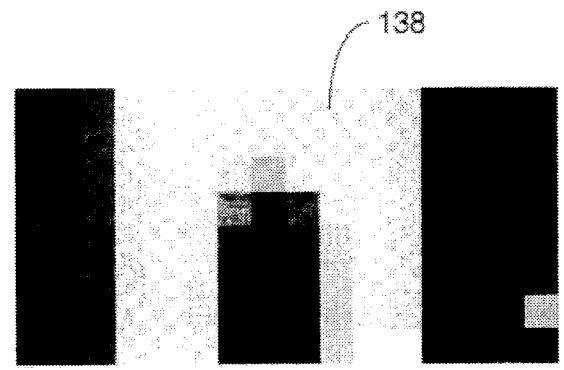

The prototype sensors were tested by directing x-rays 2 from a molydenum-anode x-ray source 4 through various targets 6 onto sensor 1. X-ray images acquired with one of these prototype sensors are displayed in FIGS. 13A and 14B. FIG. 13B is an x-ray image of a portion of a wire mesh screen 132 depicted in FIG. 13A. FIG. 14B is an x-ray image of a portion of the eye of a needle 136 depicted in FIG. 14A. Initial results indicate that our prototype sensors have a nominal response of approximately 50 electrons per x-ray photon and a nominal rms dark noise approximately 400 electrons which translates to eight x-ray photons of dark noise.

CMOS TECHNOLOGY

An important feature of this invention is its use of CMOS (complimentary metal oxide semiconductor) fabrication technology. The CMOS technology offers very good performance with regard to speed, power consumption, and leakage currents; and it is very flexible since it allows the circuit designer to combine transistors of both p-type and n-type polarities on the same integrated circuit. CMOS allows both analog and digital circuits to be fabricated on the same piece of crystalline silicon, including not only the array 9 of pixel circuits 11 but virtually all of the readout electronics, including shift registers 44, sample-and-hold circuits 54, analog switches 56, and even analog-to-digital converters. Because CMOS is a very popular and mature technology, CMOS fabrication processes are relatively inexpensive and are readily available in many variations at most semiconductor foundries.

One of the available CMOS processes is an older process allowing minimum feature sizes of two microns. For this process the photolithographic masks with the circuit patterns are projected onto the entire surface of the substrate wafer of single-crystal silicon instead of onto smaller portions of the wafer, as with more modern processes capable of smaller feature sizes. Wafer diameters of four inches may presently be used with this process, and whole-wafer projection using six inch diameter wafers will soon be available. Thus, our prototype sensor array can be scaled up to provide much larger sensors as needed for various types of medical x-ray imaging.

This CMOS design is suitable for an n-well fabrication process. This specification refers to the ion implantation process used to create islands of doped silicon on the substrate. These islands have majority charge carriers opposite in type to the majority charge carriers of the substrate. Thus, an n-well process creates islands of n-type material in a substrate of p-type material. A p-well process creates p-type islands in an n-type silicon substrate. The difference in the circuits relates to whether the circuit voltages are positive or negative with respect to the substrate. For our first full scale device we will use the n-well process in a p-doped wafer because our small prototype array is an n-well device and performs very well. However, we could also use an n-doped wafer with p-wells and our invention is intended to cover both approaches.

Circuit Defect Strategy

One object of this invention is to provide a large-scale sensor with a square or rectangular image format large enough to cover the majority of a four-inch or six-inch diameter silicon wafer. A preferred embodiment of this large-scale sensor 190, shown in FIGS. 15A and 15B, occupies an area of 46 square centimeters. It is not obvious that integrated circuits this large can actually be produced at low cost. The process yield would be very close to zero for a normal CMOS design of this size, since the probability for serious defects is very high for large-area chips. These defects arise from unavoidable dust and dirt particles which find their way onto the surface of the masks or the wafer in spite of the stringent cleanliness requirements.

Figure 15A:
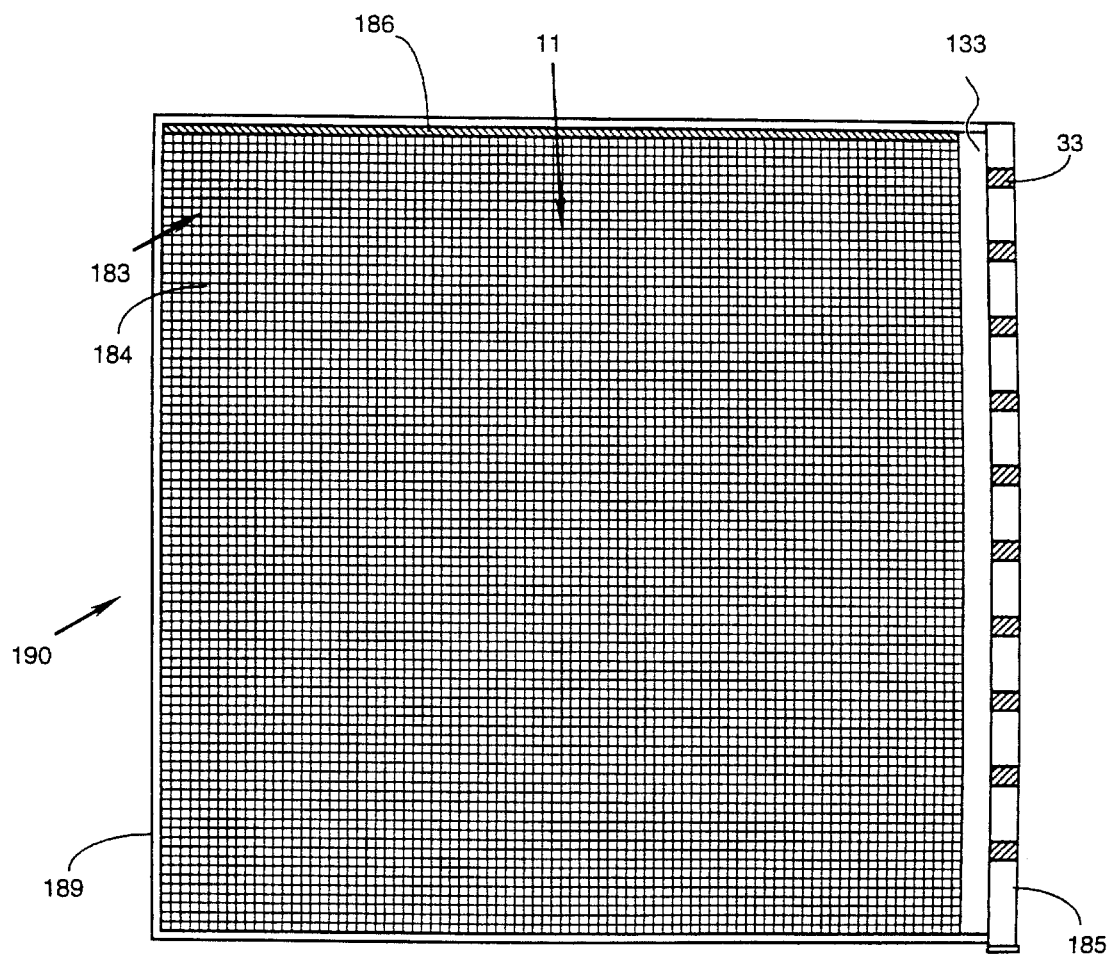
FIGS. 15A and 15B are drawings showing the principal elements of an image sensor presently being fabricated by the inventors.

The basis of the design strategy for the full-scale sensor is suggested by the observation that the area occupied by our integrated circuit can be divided into two regions of differing nature; one region is the very large area occupied by the pixel array 183, and the other region is the smaller region, less than one percent of the total, occupied by the readout circuits 133 and 186 at the edges of the array (see FIG. 15A). The occurrence of defects in the region of the readout circuits 133 and 186 will probably disable the entire integrated circuit. However, the probability for any defects in this region is quite small because the area of the region is small; and thus normal care in design such as keeping circuit features well separated and avoiding unnecessary or vulnerable components will be sufficient for this region. On the other hand, because the occurrence of defects in the large region of the pixel array 183 is almost certain, then we must accept their inevitability and take steps to minimize their effect on the performance of the device.

Circuit defects will be of two main types: defects resulting in breaks in conducting lines, and defects causing electrical shorts between lines or components. In the pixel array 183 the effect of the first type of defect is limited to loss of function for the individual pixels 184 served by the defective feature, either one pixel or part of a row or column of pixels. However, the second type of defect in the pixel region can lead to loss of function for all of the pixels in the array if the short circuit causes large currents to flow in essential parts of the peripheral readout circuitry 133 and 186. Therefore, part of our strategy is to eliminate opportunities for catastrophic damage by adding buffer amplifiers 50 or resistors 51 (see FIG. 16) to most of the lines connecting the pixel region to the peripheral circuits in order to limit the current drain on the external circuits to tolerable levels in the event of a few short-circuit defects. For example, a defect which shorts out one of the reset lines to the grounded substrate would wipe out the entire reset capability of the readout circuitry if the circuit were designed with all the reset lines connected in parallel directly to a common bus. Therefore, we connect the reset bus 66 to the reset lines 29 through buffers 50 (FIG. 6) or resistors 51 (FIG. 16) to isolate the control circuitry on the edge of the array from problems downstream in the pixel region. For the same reason, the readout select lines 53 in the pixel region are isolated with buffers 50 from the select shift register 186 on the edge of the array. Otherwise, damage to one of the readout select lines in one of the pixels could disable the shift register controlling the entire readout process. There is a similar problem with providing a connection to a supply-voltage bus in each pixel, since a pixel defect shorting out the supply-voltage line could wipe out the supply voltage for all pixels. Therefore, the voltage used by the active elements in the pixels must be provided by some less direct means. The pixel circuits 11 do not have power supplied by a separate power supply line. Instead, the pixel power is provided through column output lines 28, which are connected to current source transistors 110 in the sample-and-hold circuits 54 (see FIG. 8) at the edge of the array.

In spite of the precautions, the effect of defects will still be considerable; defects will probably cause loss of function in all pixels in some individual rows or columns and might even destroy adjacent pairs of rows and columns, but the remaining pixels will still operate properly. Missing individual pixels and even missing rows or columns can be corrected by having the computer 23 assign values to the missing pixels by interpolation between the values of the neighboring pixels, and very little diagnostic value is lost. For clusters of missing pixels or pairs of missing rows or columns there could be significant loss of data, and it may be necessary to make two exposures in succession with a small diagonal shift of the entire sensor 190 of perhaps 5 or 10 pixels between the two exposures. The computer 23 will then combine the two exposures into a single image and the single image will have very few missing pixels.

The use of two successive exposures with the small diagonal shift will also assist with the problem of combining a number of these sensors into a full format sensor. The full format sensor will undoubtedly have gaps which are non-responsive to x-rays between the individual sensors. If the double-exposure technique will take care of missing rows or columns, it will also permit us to fill in the gaps with x-ray information between the individual sensors. Another benefit of the double-exposure technique is that it permits the construction of a more efficient device for x-ray scatter rejection, as explained below.

COMMERCIAL 1024×1024 IMAGE SENSOR

Figure 15B:
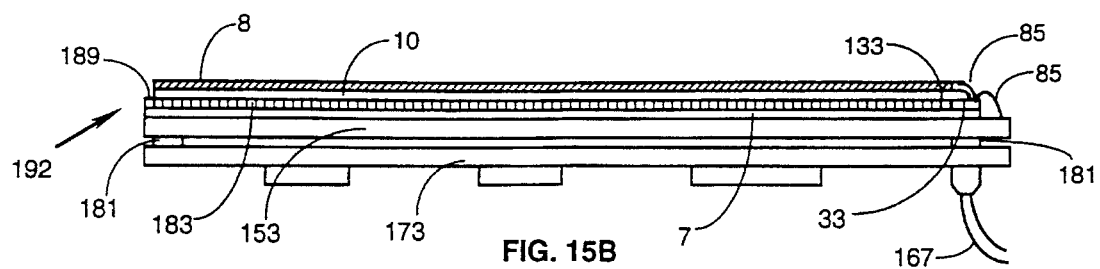
Figure 16:
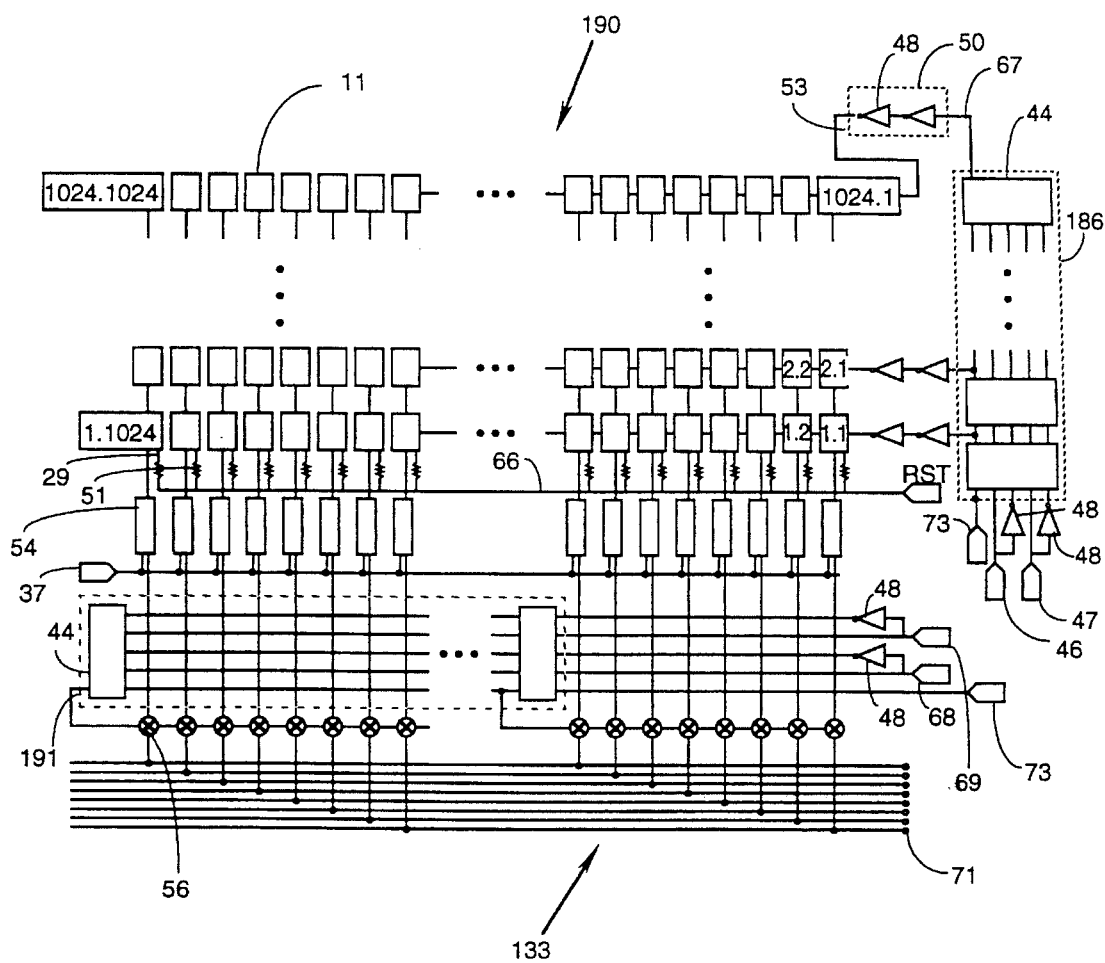
FIG. 16 is a schematic diagram of the electronic readout array in the second preferred embodiment.

The second preferred embodiment of the invention, shown in FIGS. 15A, 15B, and 16, provides an electronic readout array 190 with a 1024×1024 pixel array 183 of pixel circuits 11, and readout circuitry 133. The size of each pixel circuit 11 is 66 microns ×66 microns resulting in an image format of 6.75 cm×6.75 cm. An outline drawing of readout array 190, as in our prototype, is shown in FIGS. 15A and 15B. Row-select shift register 186 occupies a width of approximately 100 microns (less than two pixels) and extends along the entire length of one edge of the pixel array 183. The electronic readout circuit 190 has a very thin (less than 250 micron) edge 189 around three of the sides. The readout circuitry 133 requires a relatively small area, approximately 0.1 cm×6.75 cm, and wire bond pads 185 are provided at this edge to make control, output, and power connections.

FIG. 16 shows a schematic diagram of the electronic readout array 190. Row-select shift register 186 contains 1024 flip-flops 44, one for each row, and controls the row selection for readout purposes. Readout circuit 133 contains a sample-and-hold circuit 54 and a bilateral switch 56 for each of the 1024 columns of pixel circuits 11. The column-select shift register 19 1 contains 128 flip-flops 44, one for each set of eight columns. The output from each flip-flop 44 output controls eight bilateral switches 56 which simultaneously connect groups of eight outputs of sample-and-hold circuits 54 to eight parallel output lines 71. Voltages from output lines 71 are buffered and routed to data acquisition electronics 20. The circuit diagrams of the flip-flop 44, sample-and-hold circuits are shown in FIGS. 7 and 8 respectively.

Our eight separate outputs provide some important benefits. We have provided for a 125 milliseconds readout time for entire array. This would require a data rate of 8 MHz for one million pixels if we have only one output line. This high data rate would require the output driver to supply large currents needed to rapidly charge and discharge the parasitic capacitance of the output line 71. The large currents require a wide output line 71 running the length of the edge of the readout circuitry 133, which increases the parasitic capacitance of the output line 71. The incorporation of eight parallel output lines 71 running at one eighth of the total data rate reduces the current and therefore the width of each line 71. The particular configuration for the eight outputs shown in FIG. 14 results in a simple topography for the network of crossing lines and also facilitates pixel readout in a normal raster scan sequence with a fast eight-to-one analog multiplexer and a fast analog-to-digital converter in the data acquisition circuitry 20 external to the electronic readout array 190. If instead the readout scheme were not sequential along each row, then the normal cross-talk inherent in fast analog-to-digital converter circuits would be between non-neighboring pixels and would result in noticeable ghost images.

The reset circuitry shown in FIG. 16, is similar to the reset circuitry of the small-scale prototype array, except that the reset buffers 50 shown in FIG. 5 are replaced with polysilicon resistors 51. This change allows the option of turning off the reset transistors 26 with a reversed gate-to-source voltage (−2 Volts for this embodiment) in order to avoid leakage of charge through the reset transistors 26.

Each electronic readout array 190 is fabricated, on a four-inch diameter wafer of crystalline silicon 7, using the CMOS fabrication methods previously described. In order to facilitate close butting of the arrays, each wafer is then cut with a diamond saw to provide narrow border regions 189 on the three sides without the wire bond pads 185. Each electronic readout array 190 is attached to a chip carrier 153, as shown in FIG. 15B, which is fabricated from an electrically insulating, thermally stable material such as aluminum oxide ($Al_2O_3$) or FR4 circuit board material. Chip carrier 153 is fabricated with electrically conductive routing lines, and electrical connections from readout array 190 to chip carrier 153 are made with wire bonds 157. Readout array 190 is coated with amorphous selenium 10 and then with conductive electrode 8 which is electrically connected to readout circuitry 190 with wire bond 157. The chip carrier 153 is electrically connected to circuit board 173 which contains circuitry to amplify the voltages at output lines 71, analog-to-digital converters to convert the analog voltages to digital data, clock and control circuitry to supply clock and data signals to shift registers 191 and 186, control signals for the sample-and-hold circuits and the reset function, digital transmission circuitry to transmit the digital data to computer 23, and power circuitry to supply electrical power to the readout array 190. The chip carrier 153 and circuit board 173 are approximately the same size as the electronic readout array 190 in order to facilitate butting of the image sensors to form a full format image sensor.

FULL FORMAT IMAGE SENSOR

One object of this invention is to provide a high-resolution digital x-ray image sensor large enough to image large areas of the human body, such as the full breast, for example. The two standard film sizes for film/screen mammography, 18 cm×24 cm and 24 cm×32 cm, approximate the preferred size for a full-format digital sensor for the mammography application. The CMOS process constrains the maximum size of a monolithic digital sensor to 6.75 cm×6.75 cm for a four inch diameter wafer (or 10.1 cm×10.1 cm for a six inch diameter wafer). This size constraint necessitates combining several of these smaller image format sensors to form a full format sensor.

Figure 17A:
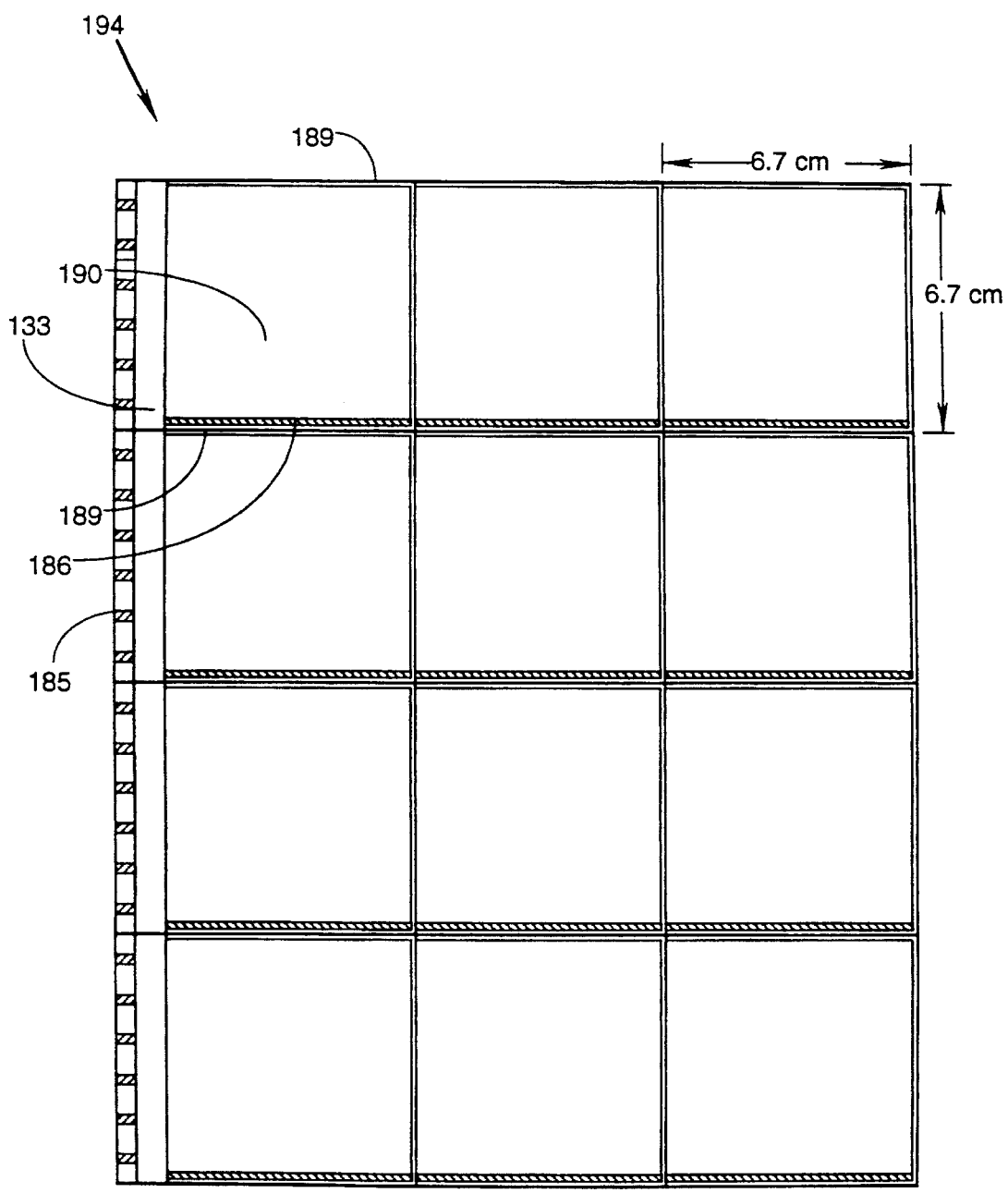
FIGS. 17 and 17B show a method for combining multiple image sensors in order to produce a larger format imaging sensor.
Figure 17B:
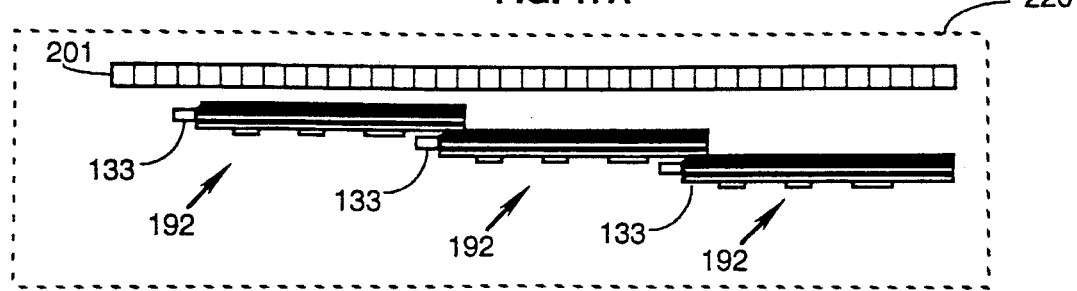

FIGS. 17A and 17B show a preferred approach for fabricating a full-format image sensor. Twelve of the 1024× 1024 pixel image sensors are combined in a 3×4 array to produce an image area of 20 cm×27 cm containing 12.6 million pixels in a 3072×4096 pixel array. We first butt four image sensors together in a row. We then shingle three of these sensor rows together with the readout circuitry 133 and wire bond pads 185 of each successive row lying underneath the previous row as shown in FIG. 17B. The digital signals from each of the twelve image sensors are routed through cables 167 to data acquisition electronics 20 comprising digital memory for data storage and custom timing and control electronics attached to a 90 MHz Pentium based computer system. The preferred full format image sensor 194 shown in FIGS. 17A and 17B, has gaps 186 and 189 which are non-responsive to x-rays between adjacent image sensors 190.

Figure 18:
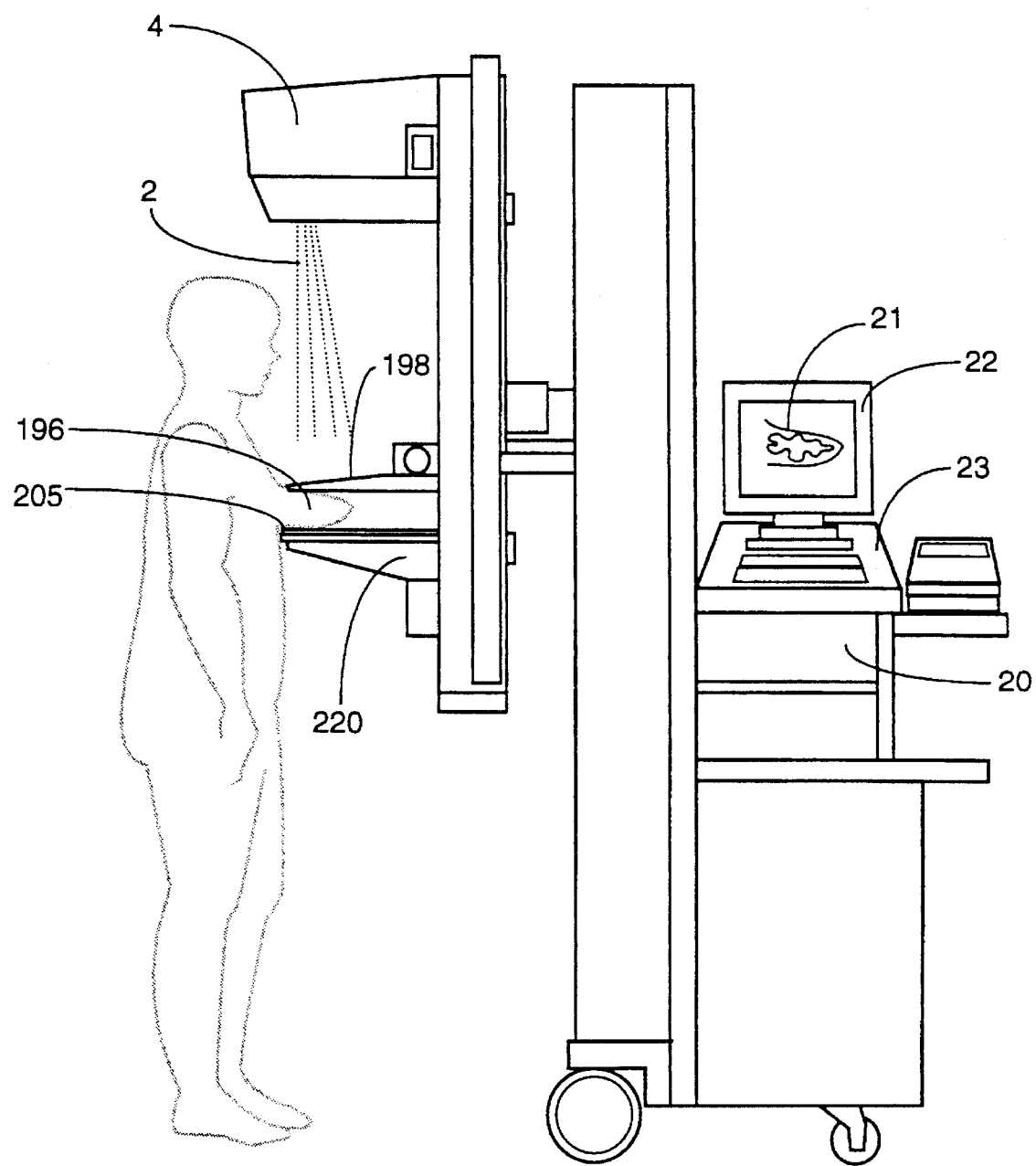
FIG. 18 show the invention used in the mammography application.

FIG. 18 shows our full format image sensor incorporated in a digital x-ray mammography device. This device includes sensor/grid assembly 220 shown in FIG. 17B which incorporates the full format digital image sensor 194 and x-ray anti-scatter grid 201. X-ray source 4 directs x-rays 2 through breast 196 which is compressed between compression paddle 198 and breast tray 205. The x-rays 2 pass through breast tray 205 to the assembly 220 containing x-ray grid 201 and full format image sensor 194. Image data 21 is acquired with data acquisition electronics 20 and appears on computer monitor 22.

Anti-Scatter Grid

For most x-ray imaging situations, a large amount of radiation scatters from the object being imaged. These scattered x-rays contain no usable imaging information but can have an intensity equal to or greater than the unscattered primary radiation containing the image information. If this scattered radiation is allowed to reach the imaging sensor, it will not only fog the image and reduce the contrast but, because of the random statistical nature of the x-ray production, absorption, and scattering processes, the scattered radiation will also add random fluctuations on top of the normal random fluctuations contained in the image-bearing primary x-rays. The signal-to-noise ratio can be degraded to such an extent that it is necessary to increase the x-ray dose to the patient 100% or more in order to compensate for the degradation.

For medical screen/film images the scatter is usually reduced by means of the x-ray grid or Bucky, a device stationed below the scattering object and composed of multiple x-ray absorbing slats oriented to allow passage of only those rays on paths consistent with emanation from the x-ray source and stopping those rays with directions altered by angular scattering. This grid introduces serious problems of its own: the pattern of the grid can appear on the image, and the grid blocks or absorbs a substantial portion of the primary beam. The usual solution to the problem is to use very fine and very expensive grids built up of many alternate layers of low-absorption and high-absorption materials with the layer planes angled toward the location of the x-ray source. For low-resolution requirements, such as chest x-rays, these grids are usually stationary; and for high-resolution requirements, such as for mammography, the grids are moved during the exposure to reduce the imaging of the grid. Design trade-offs for optimizing these grids for various applications result in specialized combinations of slat spacing, thickness, and width to achieve a performance compromise involving incomplete scatter cleanup in exchange for less loss of the primary beam. This loss of the primary beam can be as much as 50% and often nullifies most of the signal-to-noise benefit of the scatter reduction.

A preferred embodiment of our invention includes an anti-scatter grid designed to take advantage of opportunities presented by features of the present invention. The grid consists of an array of tantalum or tungsten ribbons 0.002 inch thick by 1 inch wide and spaced by 0.2 inches. These ribbons are stretched on a frame holding the ribbons planes parallel to the primary x-rays. This grid would block most of the scattered radiation but could, for very flat and accurately-angled ribbons, block only 1% of the primary x-rays. Instead of providing independent motion of the grid assembly in order to reduce the imaging of the grid, this grid assembly is fixed to the x-ray sensor stationed just below the grid assembly. The pixels blocked by the grid ribbons are treated as missing pixels, and these missing pixels are filled in with the technique of the double exposure with a diagonal shift in the same manner as the pixels missing in the gaps between the butted arrays and in the defect-damaged rows and columns. Thus we have a means of providing an inexpensive anti-scatter grid having nearly ideal performance.

IMAGE ACQUISITION AND PROCESSING

Initializing Electronics and Software

Embodiments of the present invention are initially characterized to identify hardware imperfections including dead or weakly responding pixels in each sensor 192, gaps between the different image sensors 192, spatially varying illumination of the x-ray source 4, and gain variations of the pixels 11. The characterization information of the hardware imperfections is used to process the breast image data produced by the mammography system in order to maximize the final image quality.

The characterization procedure requires the acquisition of eight dark field images with the x-ray source 4 turned off and eight white field images, acquired with a 2 cm thick sheet of Lucite on the breast tray 205 and illuminating the full format sensor 194 with x-ray source 4. A dark field image is subtracted from a white field image to produce a residual frame and eight of these residual frames are averaged to form one calibration frame. Dead or weakly responding pixels in each sensor 190, and gaps between the different sensors 190, defined as having greater than 15% variation in luminance, are identified as defective pixels in the calibration image. Defective pixels are corrected in the calibration image by interpolation of eight nearest neighbors for point defects and six nearest neighbors for column or row defects. The calibration image is then stored in the computer 23 as an array of pixel values and the positions of each defective pixel are stored as a defect map. We also average the pixel values in the calibration image and store this single mean value. For this preferred embodiment, there are up to 12,582, 912 (3072×4096) pixel values.

Image Data Acquisition

The preferred x-ray source 4 for the mammography application is a molybdenum-anode x-ray tube with a 50 micron thick molybdenum filter, which produces an x-ray primarily consisting of two sharp spectral lines at 17.9 keV and 19.5 keV. A second preferred source 4 for the mammography application is a tungsten-anode x-ray tube with a 50 micron thick silver filter, which produces an x-ray spectrum centered around 26 keV. The typical x-ray dose for the mammography application is 200 millirads per image.

A preferred procedure for obtaining a mammogram is as follows: Two raw x-ray images of the breast 196 are sequentially acquired. The first image is acquired using one half of the x-ray dose presently used for film/screen mammography. This image has a number of gaps 186 and 189 between sensors 192, pixel columns and rows which are shadowed by x-ray grid 201, and dead pixels in each sensor 190. The entire assembly 220, comprised of full format sensor 194 and x-ray grid 201 is moved obliquely to a new position which is displaced ten pixels in the x-direction and ten pixels in the y-direction. A second raw image is acquired with sensor/grid assembly 220 at the new position, using the same x-ray dose as used for the first image. The two images are stored in computer 23. A single dark image with the same integration time as the raw images is also acquired and stored.

Producing Images from Image Data

The two raw images are corrected for gain variations of the sensor pixels and spatial variations of the x-ray source 4 by a procedure commonly known as "flat fielding." The value for each pixel in the corrected image is obtained by subtracting the dark image pixel value from the corresponding pixel in the calibration image, and then multiplying by the calibration image mean value.

The two corrected images will exhibit a slight difference in the average pixel values due to slight variations in the x-ray exposure. To correct for this effect, we normalize image 2 to image 1 by multiplying all the pixel values in the second corrected image by the ratio of the mean values of the first and second images. All known defective pixels and pixels obscured by the grid slats are assigned values of zero in the pixel-value arrays, and both arrays are given extra zero-value pixels to fill in the gaps between the sensors 194. Then the two pixel-value arrays are shifted (in the computer 23) relative to each other to account for the mechanical shifting of the sensor/grid assembly 220 between x-ray exposures and are summed pixel-by-pixel to form a composite image whenever a zero-value dead or defective pixel is added to a good pixel value, the value of the good pixel is doubled to correct for the missing contribution to the sum. When both pixel values forming the sum are zero, then the composite pixel is assigned a value which is interpolation of the values of the nearest neighbor pixels. The resulting composite image will show no lines representing the grid or the gaps between the sensors.

Image Enhancement

The final composite image of the full breast 196 is processed in the computer 23 in order to optimize the contrast between features in the breast. The preferred image enhancement procedure involves a preferential enhancement of the fine detail in the image while preserving the large-area contrast. The enhancement procedure calculates the natural logarithm transform of the pixel values of the image to reduce the contrast differences. The image, an enhancement procedure called "unsharp masking" is then applied to the image. This procedure is described in Section 7.4 of "Fundamentals of Digital Image Processing", by Anil K. Jain, Prentice Hall, N.J., 1989.

In addition, while viewing the image, the radiologist is able to adjust the parameters controlling the overall contrast in order to selectively enhance the visibility of features in different portions of the image.

ALTERNATE EMBODIMENTS

While the above description contains many specific details the reader should not construe these as limitations on the scope of the invention, but merely as exemplifications of preferred embodiments thereof. Those skilled in the art will envision that many other possible variations are within its scope.

For example we could place two of the pixel circuits 11, each depicted in FIG. 5, side by side at each pixel location. Two capacitors 78, each connected to the electrode 14 through separate switches, can store two consecutive images, without the necessity of an intermediate readout. Another embodiment involves the addition of analog-to-digital converters to each column of the electronic readout array 12.

An alternate fabrication method for the electronic readout array 190 involves the use of a six inch diameter silicon wafer. This wafer would provide a 1536×1536 array of our 66 micron pixels 11 resulting in a 10 cm×10 cm image format. A full format 20 cm×30 cm image sensor can be fabricated by combining six of the 10 cm×10 cm image sensors in a 2 ×3 array.

Figure 19:
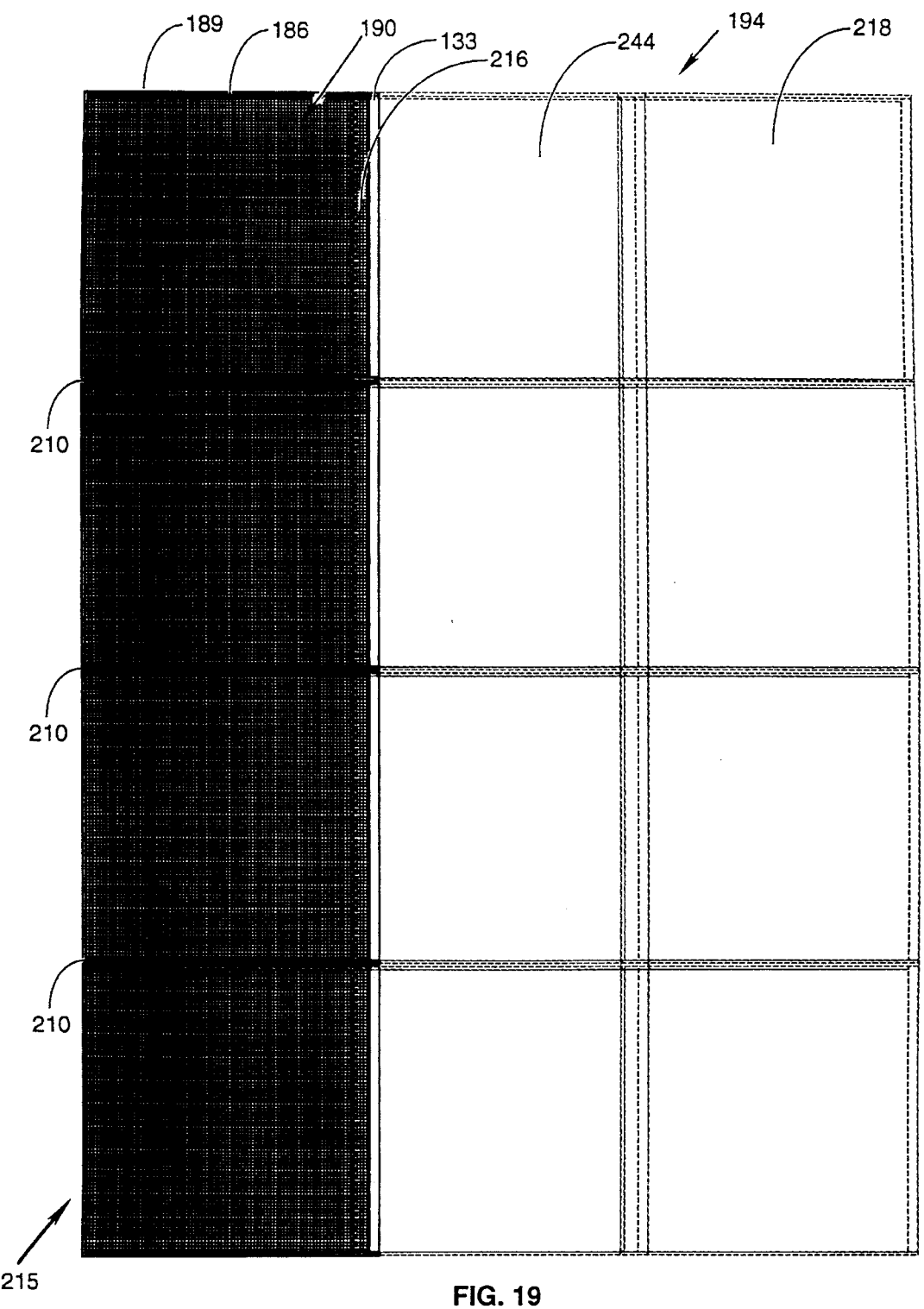
FIG. 19 shows a method of using a strip of image sensors to sequentially image different areas of an object.

Instead of combining 12 sensors in a 3×4 sensor array to form a full-format sensor, an alternate embodiment involves the combination of four sensors 190 in a row as shown in FIG. 19. This provides a 1024×4096 pixel x-ray image sensor assembly 215 comprising an image area of approximately 6.7 cm×27 cm, with three gaps 210 approximately 1 mm×6.7 cm (approximately 15×1024 pixels) which are missing x-ray information. This sensor assembly 215 is stepped to two separate slightly overlapping positions 244 and 218 across the desired image region with an x-ray exposure at each position, and the data from the exposures are combined by the computer 23 to form a full-format image. An additional small diagonal motion in between two one-half dose exposures at each of the step positions may be employed to fill in the missing information in the gaps as well as the other missing pixels, as discussed earlier. The three strips of digital x-ray image information can be combined to form a single image by utilizing stitching algorithms disclosed in patent application 08/344,141. These algorithms provide means to register overlapping images using correlation techniques and to combine the images with the blending of the overlap regions. As the sensor assembly is stepped to a new position, the tube assembly with its beam-limiting aperture is rotated about the fixed x-ray source point in order to follow the sensor assembly. The aperture limits the extent of the x-ray beam to just the sensitive area of the 1×4 sensor assembly and prevents the patient from being dosed with x-rays which do not contribute to the image.

This 1×4 array of sensors is particularly well suited to the ribbon grid concept discussed previously. In this embodiment the ribbons of tantalum or tungsten must be stretched in the direction of the principal stepping motion so that the ribbon planes remain parallel to rays fanning out from the x-ray source in each of the step positions. Since this motion direction is parallel to the short dimension of the sensor assembly, then we derive an additional benefit from the fact that the ribbon segments are short and are thus more likely to remain flat and accurately angled in accordance with the constraints at the ends of the segments. Nearly perfect flatness and angular alignments are required to minimize the number of pixels obscured by the grid. The signal values of these obscured pixels will be restored by the technique of the double exposure with a diagonal shift, as discussed above, but the overall signal-to-noise ratio in the image will suffer if too many pixels have acquired their values with only one-half of the total x-ray exposure. Furthermore, this orientation of the ribbons is the best choice for reduction of scatter. The scattered x-rays have paths with origins in the elongated region where the 1×4 aspect-ratio fan of primary x-rays intercepts the object being imaged. The scatter in directions nearly parallel to the ribbon planes is not stopped by the grid, but for this configuration that scatter is limited to a small range of angles controlled by the short dimension of the region of origin of the scattered rays. There are many more scattered rays having direction components in the direction of the long dimension of the sensor array, but most these rays will be stopped by the grid ribbons. This grid design coupled with the stepped detector assembly is more effective at removing scattered radiation than conventional grids presently being sold for mammography and is much better at preserving the intensity of the unscattered rays.

In another approach we would use of a single 6.75 cm×6.75 cm selenium-coated image sensor in a mammography unit. This x-ray sensor is moved to sequentially image different areas of the breast. These slightly overlapping images are then stitched together in the computer using a correlation technique to form a full seamless image of the full breast.

An alternate embodiment involves the use of a very small dose of x-ray exposure to at least a small portion of a target 6, such as a breast, for example, in order to determine the optimal x-ray exposure level for the final image. The optimal x-ray exposure depends on the breast size and composition. This pre-exposure x-ray pulse can be applied to compressed breast 196 for approximately two milliseconds duration, immediately before the full x-ray exposure. The pre-exposure pulse can be applied to the full breast or to a portion of the breast by using an aperture located near the x-ray source 4. The digital information can be acquired from at least a portion of the full-format image sensor 194 and used to determine the full x-ray exposure level. One embodiment of the pre-exposure pulse involves acquiring digital information from a 100×100 array of pixels 11 located in the approximate center of the area of the final image 21 occupied by the breast 196. The average of the digital values from this 100×100 array of pixels is then used to determine the exposure level. Another alternate embodiment involves using three 100×100 arrays of pixels, separated so as to sample various portions of the breast 196. A weighted average of the digital information from these three arrays is then used to determine the exposure level.

An alternate embodiment of the pre-exposure x-ray pulse involves the use of at least two such pulses with different x-ray energies. The x-ray energy of the two pulses can be varied by adjusting the voltage applied to the x-ray source 4 or by changing the x-ray filter, from silver to rhodium, for example, between pulses. This information is then used to determine the optimal x-ray energy and x-ray dose for the x-ray image of the breast.

An alternate embodiment of the invention is a chest x-ray device with 125 micron square pixels on a 30 cm×45 cm image area. This image format can be achieved by combining twelve 10 cm ×10 cm image sensors in a 3×4 sensor array, in a manner similar to that depicted in FIGS. 17A and 17B, or by combining four 10 cm×10 cm sensors in a row, and sequentially stepping the assembly to three different positions to acquire the full format image.

Chest x-ray images typically require x-rays with photon energies centered at 60 to 70 keV. The selenium layer 10 will be 1200 microns thick to absorb most of these incident x-rays. Alternatively, the radiation absorbing layer 10 would be comprised of lead oxide, which has an absorption constant which is four times higher than selenium. A 300 micron layer of lead oxide will absorb most of the x-rays between 60 and 70 keV.

An alternate embodiment of the invention is a fluoroscopy device. The preferred embodiment has spatial resolution and x-ray spectrum requirements similar to the chest x-ray device. The preferred embodiment of the fluoroscopy device operates at a ten hertz frame rate and has a 10 centimeter square image area. The x-ray dosage per image frame is limited to a few millirads in order to keep the total x-ray dose per exam at a reasonable level.

The invention can be used to image electrical circuit boards. Preferred radiation for this application is 60–70 keV x-ray photons, and 1200 microns of selenium are required to absorb most of the x-ray photons. The preferred embodiment has 25 micron square pixels over a 3 cm square image area.

An alternate embodiment for the invention is a sensor for x-ray computed tomography (x-ray CT) imaging devices. This embodiment utilizes a fan-beam x-ray source which is detected by a partial arc of x-ray detectors located opposite the x-ray source. The preferred sensor includes 480 pixel elements, each element two millimeters square, arranged on a 46 cm radius circular arc. Each sensor element has a 1200 micron thick layer of selenium to absorb most of the 70 keV x-ray photons. The x-ray source and sensor rotate around a target and x-ray information is acquired from all the pixel elements for discrete angular locations of the rotating source and sensor. The x-ray information is used in mathematical reconstruction algorithms to form a tomographic image of the target using well known techniques.

We can use the concepts disclosed herein for detection of ultraviolet radiation. Read-out arrays in the ultraviolet spectrum from 250 nm to 400 nm require a selenium coating only a few microns thick to absorb most of the ultraviolet photons. The selenium coating covers both the CMOS array and the readout electronics. The CMOS arrays are then coated with a 100 angstrom thick layer of silver which provides over 95% transmission of UV photons in the range from 250 nm to 400 nm. Additional silver is coated over the readout electronics in order to provide a wire bonding surface for making an electrical connection to an external pin on the chip carrier. For special applications we would also apply the principles of this invention with other radiation sources such as alpha or beta radiation.

Photoconductive insulating materials other than selenium can be used as the absorbing layer. Preferably the thickness of the layer will be large enough to absorb most of the radiation. Other materials include silicon, lead oxide, lead sulfide, zinc oxide, zinc sulfide, cadmium telluride, and diamond film.

Selenium has a photoconductive response in the spectral range from x-rays to visible light, becoming less responsive in the spectral region beyond 500 nm. The addition of 70% tellerium to selenium raises the photoconductive response in the visible region and extends the response to 800 nm.

Accordingly, the reader is requested to determine the scope of the invention by the appended claims and their legal requirements, and not by the examples which have been given.

We claim:

1. An imaging device for producing images from electron-hole producing radiation comprising:
   A. at least one solid state radiation detection unit comprising
      1) a wafer comprised of doped single crystal silicon,
      2) a plurality of complementary metal oxide semiconductor pixel circuits incorporated into said single crystal silicon to form an array, defining an array of pixel circuits, each of said semiconductor pixel circuits defining a pixel and comprising:
         a) a charge collecting pixel electrode,
         b) a pixel capacitor electrically connected to said charge collecting electrode so as to store charges collected by said charge collecting electrode,
         c) a charge measuring transistor means comprising at least one transistor for permitting a measurement of charge stored on said pixel capacitor,
      3) a radiation absorbing layer comprised of a photoconductive electrically insulating material covering said array of pixel circuits, said insulating material being photoconductive on exposure to said electron-hole producing radiation,
      4) a surface electrode layer comprised of electrically conducting material deposited on said radiation absorbing layer, said electrode layer being at least partially transparent to said radiation, and
      5) a high voltage source means for establishing an electrical field across said radiation absorbing layer and between said surface electrode layer and said charge collecting electrodes;
   B. a pixel charge measurement means for making said measurements of charges stored on each of said pixel capacitors via said measuring transistor means,
   C. a data acquisition means for acquiring and storing data derived from said charge measurements,
   D. a computer means for computing at least one image from said data.

2. An imaging device as in claim 1 wherein said electron-hole producing radiation comprises x-ray radiation.

3. An imaging device as in claim 1 wherein said electron-hole producing radiation comprises ultraviolet radiation.

4. An imaging device as in claim 1 wherein said electron-hole producing radiation comprises particle radiation.

5. An imaging device as in claim 1 and further comprising a monitor for display of said image.

6. An imaging device as in claim 1 and further comprising a printer for printing said image.

7. An imaging device as in claim 1 wherein each pixel capacitor is comprised of an insulating oxide layer sandwiched between two heavily doped polycrystalline silicon layers.

8. An imaging device as in claim 7 wherein said oxide layer is $SiO_2$ glass.

9. An imaging device as in claim 1 wherein each charge collecting pixel electrode is comprised of aluminum.

10. An imaging device as in claim 1 wherein each measuring transistor means comprises at least two field effect transistors arranged in an electrical circuit so as to permit non-destructive measurement of said charge.

11. An imaging device as in claim 10 wherein said at least two field effect transistors comprise a source follower transistor and a selection transistor.

12. An imaging device as in claim 11 wherein each pixel capacitor defines two parallel plates and each source follower transistor defines a gate and one of said plates is electrically connected to said gate.

13. An imaging device as in claim 12 wherein said each of said semiconductor pixel circuits also comprises a reset transistor means for resetting each of said pixel circuits.

14. An imaging device as in claim 13 wherein each reset transistor means comprises an electrical circuit for shorting the associated pixel capacitor to ground.

15. An imaging device as in claim 14 wherein each reset transistor means comprises a reverse back biased reset transistor.

16. An imaging device as in claim 13 wherein said photoconductive electrically insulating material comprises amorphous selenium.

17. An imaging device as in claim 16 wherein said selenium is deposited as a film.

18. An imaging device as in claim 17 wherein said film is vapor deposited.

19. An imaging device as in claim 18 wherein said selenium is alloyed with arsenic.

20. An imaging device as in claim 19 wherein said surface electrode layer comprises silver.

21. An imaging device as in claim 19 wherein said high voltage source is arranged to produce an electric field gradient in said radiation absorbing layer of between 2 and 20 volts per micron.

22. An imaging device as in claim 21 wherein said charge collecting pixel electrodes are separated from said surface electrode layer by a thickness of at least 10 microns of said photoconductive electrically insulating material.

23. An imaging device as in claim 22 wherein said array is arranged to form rows and columns and said pixel charge measurement means comprises a sample and hold circuit at each column with a shift register for selection of rows and a separate shift register for selection of columns.

24. An imaging device as in claim 23 wherein said data acquisition means comprises an analog to digital converter.

25. An imaging device as in claim 1 wherein said wafer is doped to create n-type silicon.

26. An imaging device as in claim 1 wherein said wafer is doped to create p-type silicon.

27. An imaging device as in claim 1 wherein said high voltage source means is electrically arranged so as to provide positive voltage at said surface electrode layer with respect to said charge collecting electrodes.

28. An imaging device as in claim 1 wherein said high voltage source means is electrically arranged so as to provide a negative voltage at said surface electrode layer with respect to said charge collecting electrodes.

29. An imaging device as in claim 1 wherein said at least one detection unit is a plurality of detection units.

30. An imaging device as in claim 29 wherein said plurality of detection units comprises at least one row of at least four detection units.

31. An imaging device as in claim 30 wherein said at least one row is at least three rows arranged parallel to each other.

32. An imaging device as in claim 31 wherein said at least three rows is three rows.

33. An imaging device for producing images of a target irradiated with electron-hole producing radiation comprising:
   A. A radiation source means for producing a beam of said electron-hole producing radiation, said beam defining a beam path, B. a target positioning means for positioning said target in said beam path, C. at least one solid state radiation detection unit positioned in said beam path downstream of said target, said each comprising:
   1) a wafer comprised of doped single crystal silicon,
   2) a plurality of complementary metal oxide semiconductor pixel circuits incorporated into said single crystal silicon to form an array, defining an array of pixel circuits, each of said semiconductor pixel circuits defining a pixel and comprising:
      a) a charge collecting pixel electrode,
      b) a pixel capacitor electrically connected to said charge collecting electrode so as to store charges collected by said charge collecting electrode,
      c) a charge measuring transistor means comprising at least one transistor for permitting a measurement of charge stored on said pixel capacitor,
   3) a radiation absorbing layer comprised of an electrical insulating material covering said array of pixel circuits, said insulating material being photoconductive on exposure to said electron-hole producing radiation,
   4) a surface electrode layer comprised of electrically conducting material deposited on said radiation absorbing layer, said electrode layer being at least partially transparent to said radiation, and
   5) a high voltage source means for establishing an electrical field across said radiation absorbing layer and between said surface electrode layer and said charge collecting electrodes;

D. a pixel charge measurement means for making said measurements of charges stored on each of said pixel capacitors via said measuring transistor means, E. a data acquisition means for acquiring and storing data derived from said charge measurements, F. a computer means for computing images of said target from said data.

34. An imaging device as in claim 33 wherein said electron-hole producing radiation comprises x-radiation.

35. An imaging device as in claim 34 wherein said at least one detection unit is a plurality of detection units arranged in at least one row of at least four detection units.

36. An imaging device as in claim 35 and further comprising a positioning means for moving said at least one row of detection units relative to said target.

37. An imaging device as in claim 36 and further comprising an anti-scatter grid placed between said target and said detection units.

38. An imaging device as in claim 37 wherein said anti-scatter grid is fixed with respect to said detection units.

39. An imaging device as in claim 38 wherein said computer means comprises software to generate a composite image of at least a portion of said target from a plurality of images of portions of said target.

40. An imaging device as in claim 33 and further comprising an x-ray dose limiting means for limiting x-ray dose to said target.

41. An imaging device as in claim 40 wherein said dose limiting means comprises a means for collecting pre-exposure x-ray data.

42. An imaging device as in claim 41 and further comprising spectrum selection means for selecting an x-ray spectrum based on said pre-exposure x-ray data.

43. An imaging device as in claim 33 wherein said source, said target positioning means and said at least one detection unit are configured so as to image at least a portion of a human body.

44. An imaging device as in claim 43 wherein said imaging device is utilized to image the female breast.

45. An imaging device as in claim 33 wherein said source, said target positioning means and said at least one detection unit are configured to image an electronic circuit board.

46. An imaging device as in claim 33 wherein said source, said target positioning means and said at least one detection unit are configured to provide an x-ray computed tomography device.

47. An imaging device as in claim 1 wherein said photoconductive material comprises amorphous selenium doped with tellerium.

48. An imaging device as in claim 47 wherein said electromagnetic radiation comprises visible radiation.

49. An imaging device as in claim 47 wherein said electromagnetic radiation comprises infrared radiation.

* * * * *